United States Patent
Lukasiewicz Hagai et al.

(10) Patent No.: US 10,258,652 B2
(45) Date of Patent: *Apr. 16, 2019

(54) METHODS AND COMPOSITIONS FOR TREATING AND PREVENTING MUSCLE WASTING DISORDERS

(71) Applicant: PLURISTEM LTD., Haifa (IL)

(72) Inventors: Esther Lukasiewicz Hagai, Tel Aviv-Yafo (IL); Rachel Ofir, Adi (IL); Dana Fuchs Telem, Kibbutz Kfar HaHoresh (IL)

(73) Assignee: PLURISTEM LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,537

(22) PCT Filed: Dec. 18, 2015

(86) PCT No.: PCT/IB2015/059763
§ 371 (c)(1),
(2) Date: Apr. 24, 2017

(87) PCT Pub. No.: WO2016/098061
PCT Pub. Date: Jun. 23, 2016

(65) Prior Publication Data
US 2017/0304370 A1    Oct. 26, 2017

Related U.S. Application Data

(60) Provisional application No. 62/093,412, filed on Dec. 18, 2014.

(51) Int. Cl.
| | |
|---|---|
| *A61K 35/50* | (2015.01) |
| *A61K 35/28* | (2015.01) |
| *A61K 35/32* | (2015.01) |
| *C12N 5/00* | (2006.01) |
| *C12N 5/071* | (2010.01) |

(52) U.S. Cl.
CPC .............. *A61K 35/50* (2013.01); *A61K 35/28* (2013.01); *A61K 35/32* (2013.01); *C12N 5/0062* (2013.01); *C12N 5/0671* (2013.01); *C12N 2513/00* (2013.01); *C12N 2533/30* (2013.01)

(58) Field of Classification Search
CPC ...................................................... A61K 35/28
See application file for complete search history.

(56) References Cited

U.S. PATENT DOCUMENTS 9,175,262 B2 * 11/2015 Aberman ............... A61K 35/50
2011/0171182 A1    7/2011 Abelman

OTHER PUBLICATIONS

Dezawa et al. Science, 2005, 309:314-317.*
Kawamichi et al. J. Cell. Physiol., 2010, 223:695-702.*
Indarapu et al. "Mesenchymal Progenitor Cells from Different Sources and their Potential to Differentiate In Vitro into Muscle Cells" Cell & Developmental Biology (2013) vol. 2, No. 3, pp. 1-7.
International Search Report and Written Opinion for International Application No. PCT/IB2015/059763 dated Mar. 16, 2016.
Meregali et al. "Perspectives of stem cell therapy in Duchenne muscular dystrophy" FEBS Journal (2013) vol. 280, No. 17, pp. 4251-4262.
Meregalli et al. "Advancements in stem cells treatments of skeletal muscle wasting" Frontiers in Physiology (2014) vol. 5, Article 48, pp. 1-12.
Price et al. "Stem cell based therapies to treat muscular dystrophy" Biochimica et Biophysica Acta (2007) vol. 1772, No. 2, pp. 272-283.
U.S. National Institutes of Health "Safety and Efficacy of IM Injections of PLX-PAD for the Regeneration of Injured Gluteal Musculature After Total Hip Arthroplasty" ClinicalTrials.Gov (2010), Clinical Trials Identifier NCT01525667, Retrieved from the Internet Feb. 18, 2016; URL: https:clinicaltrials.gov/ct2/show/NCT01525667?term=pluristem+muscle&rank=1.
Baracos et al., "Clinical outcomes related to muscle mass in humans with cancer and catabolic illnesses," Int J Biochem Cell Biol (2013) vol. 45, No. 10, pp. 2302-2308.
Bulfield et al. "X chromosome-linked muscular dystrophy (mdx) in the mouse," Proc Natl Acad Sci USA (1984) vol. 81, No. 4, pp. 1189-1192.
Clayton et al., "Analysis of antigen presenting cell derived exosomes, based on immuno-magnetic isolation and flow cytometry," J Immunol Methods (2001) vol. 247, pp. 163-174.
Crescitelli et al., "Distinct RNA profiles in subpopulations of extracellular vesicles: apoptotic bodies, microvesicles and exosomes," J Extracell Vesicles (2013) vol. 2, Article 20677, 10 pages.
Doehner et al., "Metabolic impairment in heart failure: the myocardial and systemic perspective," J Am Coll Cardiol (2014) vol. 64, No. 13, pp. 1388-1400.
Dominici et al., "Minimal criteria for defining multipotent mesenchymal stromal cells: The International Society for Cellular Therapy position statement," Cytotherapy (2006) vol. 8, No. 4, pp. 315-317.
Hamdani et al., "Myocardial Titin Hypophosphorylation Importantly Contributes to Heart Failure with Preserved Ejection Fraction in a Rat Metabolic Risk Model," Circulation: Heart Failure (2013) vol. 6, pp. 1239-1249.
Mathias et al., "Isolation of extracellular membranous vesicles for proteomic analysis," Methods Mol Biol (2009) vol. 528, pp. 227-242.
Mohler et al., "Nonsteroidal selective androgen receptor modulators (SARMs): dissociating the anabolic and androgenic activities of the androgen receptor for therapeutic benefit," J Med Chem (2009) vol. 52, No. 12, pp. 3597-3617.
Zembron-Lacny et al., "Sarcopenia: monitoring, molecular mechanisms, and physical intervention," Physiol Res (2014) vol. 63, pp. 683-691.
Nigro et al., "Spectrum of muscular dystrophies associated with sarcolemmal-protein genetic defects," Biochimica et Biophysica Acta (2015) vol. 1852, pp. 585-593.

* cited by examiner

*Primary Examiner* — Bin Shen
(74) *Attorney, Agent, or Firm* — Lando & Anastasi, LLP

(57) ABSTRACT

Described herein are methods of treating and preventing muscle wasting and muscle loss, using adherent stromal cells and conditioned medium produced thereby.

18 Claims, 16 Drawing Sheets

METHODS AND COMPOSITIONS FOR TREATING AND PREVENTING MUSCLE WASTING DISORDERS

CROSS REFERENCE TO RELATED APPLICATIONS

This application is a national stage application of International Application No. PCT/IB2015/059763, filed Dec. 18, 2015, which claims priority to U.S. Provisional Application No. 62/093,412, filed Dec. 18, 2014.

FIELD

Described herein are methods of treatment, prevention, and inhibition of muscle wasting disorders and muscle loss, using adherent stromal cells and conditioned medium produced thereby.

SUMMARY

Previous work has established that the act of culturing adherent stromal cells under 3D conditions produces adherent stromal cells (ASC) with heretofore undescribed properties and characteristics. Described herein are methods of using the ASC for treatment, prevention, and inhibition of muscle wasting disorders and muscle loss.

In certain embodiments, the described ASC have been prepared by culturing in 2-dimensional (2D) culture, 3-dimensional (3D) culture, or a combination thereof. Non-limiting examples of 2D and 3D culture conditions are provided in the Detailed Description and in the Examples. Alternatively or in addition, the cells have been treated with pro-inflammatory cytokines; or are a placental cell preparation that is substantially entirely fetal cells, or maternal cells; is enriched for fetal cells, or maternal cells; or is predominantly fetal cells, or is predominantly maternal cells. The term "ASC", except where indicated otherwise, may refer, in various embodiments, to adherent stromal cells either before or after incubation with pro-inflammatory cytokines.

Alternatively or in addition, the cells are mesenchymal-like ASC, which exhibit a marker pattern similar to mesenchymal stromal cells, but do not differentiate into osteocytes, under conditions where "classical" mesenchymal stem cells (MSC) would differentiate into osteocytes. In other embodiments, the cells exhibit a marker pattern similar to MSC, but do not differentiate into adipocytes, under conditions where MSC would differentiate into adipocytes. In still other embodiments, the cells exhibit a marker pattern similar to MSC, but do not differentiate into either osteocytes or adipocytes, under conditions where mesenchymal stem cells would differentiate into osteocytes or adipocytes, respectively. The MSC used for comparison in these assays are, in some embodiments, MSC that have been harvested from bone marrow (BM) and cultured under 2D conditions. In other embodiments, the MSC used for comparison have been harvested from bone marrow (BM) and cultured under 2D conditions, followed by 3D conditions.

In various embodiments, the described ASC are able to exert the described therapeutic effects, each of which is considered a separate embodiment, with or without the ASC themselves engrafting in the host. For example, the cells may, in various embodiments, be able to exert a therapeutic effect, without themselves surviving for more than 3 days, more than 4 days, more than 5 days, more than 6 days, more than 7 days, more than 8 days, more than 9 days, more than 10 days, or more than 14 days.

Except where otherwise indicated, all ranges mentioned herein are inclusive.

Except where otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the embodiments of the invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION

Figure 1:
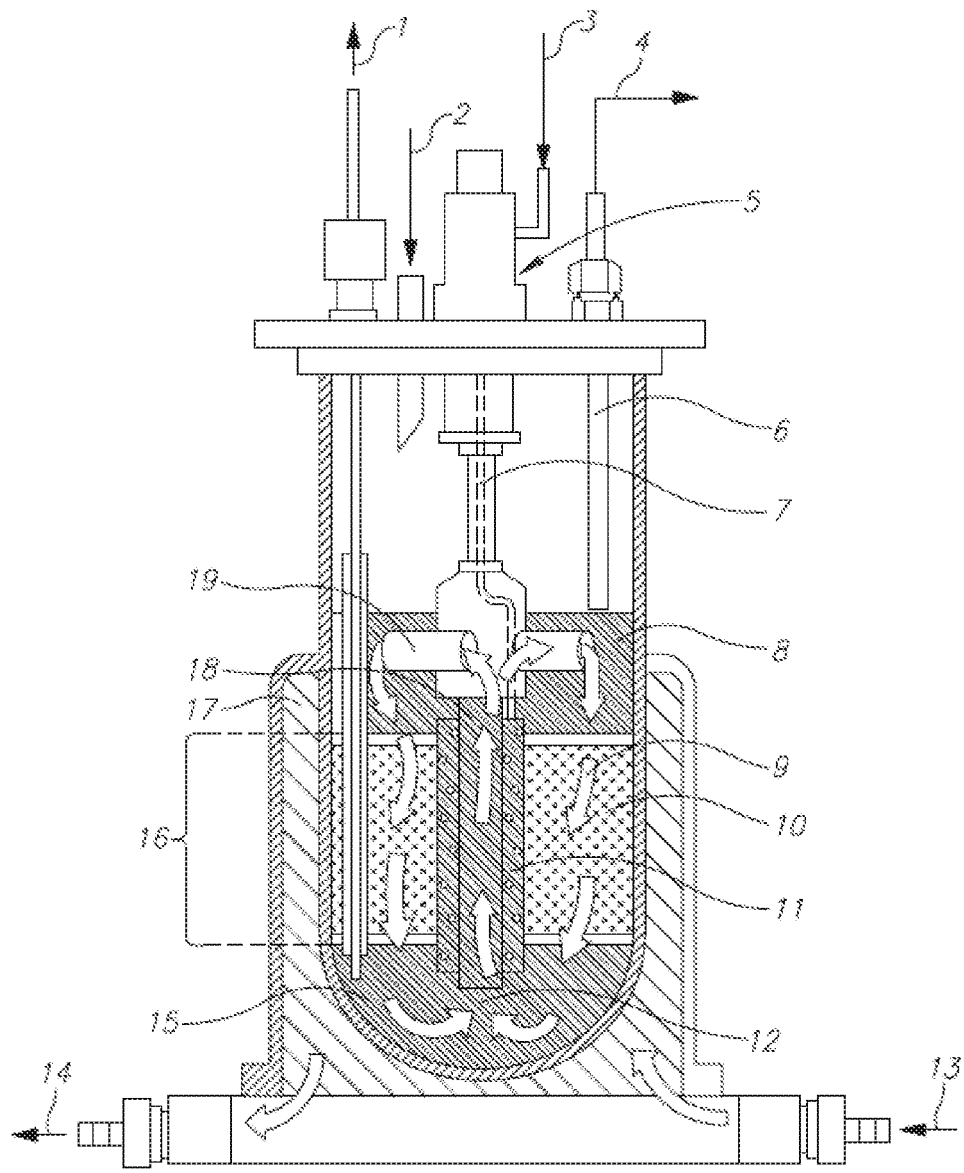
FIG. 1 is a diagram of a bioreactor that can be used to prepare the cells.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In certain embodiments, there is provided a method of treating muscle wasting syndrome in a subject in need thereof, the method comprising the step of administering to the subject a therapeutically effective amount of adherent stromal cells (ASC), thereby treating the muscle wasting syndrome in the subject. In other embodiments is provided a method of reducing muscle wasting in a subject in need thereof, the method comprising the step of administering to the subject the ASC. In still other embodiments is provided a method of reversing muscle wasting in a subject in need thereof, the method comprising the step of administering to the subject the ASC. The ASC may be derived from a placenta or, in other embodiments, from adipose tissue, or, in other embodiments, from other sources as described herein. As provided herein, administration of ASC is useful in treating and preventing muscle wasting.

In certain embodiments, there is provided a method of treating a muscle wasting disorder in a subject in need thereof, the method comprising the step of administering to the subject a therapeutically effective amount of ASC, thereby treating the muscle wasting disorder in the subject. In other embodiments is provided a method of reducing an incidence of a muscle wasting disorder in a subject in need thereof, the method comprising the step of administering to the subject the ASC. In still other embodiments is provided a method of reversing the progress of a muscle wasting disorder in a subject in need thereof, the method comprising the step of administering to the subject the ASC. The ASC may be derived from a placenta or, in other embodiments, from adipose tissue, or, in other embodiments, from other sources as described herein. As provided herein, administration of ASC is useful in treating and preventing muscle wasting disorders.

In certain embodiments, there is provided a method of treating muscular dystrophy (MD) in a subject in need thereof, the method comprising the step of administering to the subject a therapeutically effective amount of ASC, thereby treating the MD in the subject. In other embodiments is provided a method of reducing penetrance of a symptom of MD in a population, the method comprising the step of administering to the subject the ASC. In a non-limiting embodiment, the MD symptom is muscle wasting. In certain embodiments, the population is predisposed to developing MD, or in other embodiments has at least one mutation in dystrophin (DMD) or genes that regulate dystrophin expression. In still other embodiments is provided a method of arresting the progress of MD in a subject in need thereof, the method comprising the step of administering to the subject the ASC. The ASC may be derived from a placenta or, in other embodiments, from adipose tissue, or, in other embodiments, from other sources as described herein. As provided herein, administration of ASC is useful in treating and arresting symptoms of MD, for example muscle degeneration. In certain embodiments, the MD is Duchenne muscular dystrophy; or is selected from the group consisting of Becker muscular dystrophy, myotonic muscular dystrophy, congenital muscular dystrophy, Emery-Dreifuss muscular dystrophy, facioscapulohumeral muscular dystrophy, limb-girdle muscular dystrophy, distal muscular dystrophy, DMD-associated dilated cardiomyopathy (DCM), and oculopharyngeal muscular dystrophy.

In other embodiments is provided a method of reducing loss of muscle mass in a subject in need thereof, the method comprising the step of administering to the subject a therapeutically effective amount of ASC, thereby reducing the loss of muscle mass in the subject. In other embodiments is provided a method of preventing loss of muscle mass in a subject at risk thereof, the method comprising the step of administering to the subject the ASC. In still other embodiments is provided a method of reversing loss of muscle mass in a subject at risk thereof, the method comprising the step of administering to the subject the ASC. The ASC may be derived from a placenta or, in other embodiments, from adipose tissue, or, in other embodiments, from other sources as described herein.

In other embodiments is provided a method of increasing muscle mass in a subject that has a muscle wasting disorder, the method comprising the step of administering to the subject a therapeutically effective amount of ASC, thereby increasing muscle mass in a subject that has a muscle wasting disorder. The ASC may be derived from a placenta or, in other embodiments, from adipose tissue, or, in other embodiments, from other sources as described herein.

In other embodiments is provided a method of reducing a loss of muscle strength in a subject in need thereof, the method comprising the step of administering to the subject a therapeutically effective amount of ASC, thereby reducing the loss of muscle strength in the subject. In other embodiments is provided a method of preventing loss of muscle strength in a subject at risk thereof, the method comprising the step of administering to the subject the ASC. In still other embodiments is provided a method of reversing loss of muscle strength in a subject at risk thereof, the method comprising the step of administering to the subject the ASC. The ASC may be derived from a placenta or, in other embodiments, from adipose tissue, or, in other embodiments, from other sources as described herein.

In other embodiments is provided a method of treating myopenia in a subject in need thereof, the method comprising the step of administering to the subject a therapeutically effective amount of ASC, thereby treating the myopenia in the subject. The ASC may be derived from a placenta or, in other embodiments, from adipose tissue, or, in other embodiments, from other sources as described herein.

In various embodiments, the muscle wasting, loss of muscle mass, or loss of muscle strength is a result of chronic heart failure, aging, androgen deficiency, congenital causes, cancer, emphysema, diabetes, HIV-1 infection, other chronic infection, COPD (chronic obstructive pulmonary disease), myasthenia gravis, chronic renal failure, chronic liver failure, severe burns, sepsis, tuberculosis, stroke, Cushing's syndrome, cystic fibrosis, rheumatoid arthritis, Alzheimer's disease, neuromuscular diseases, other chronic disease, or chronic use of medicines, for example corticosteroids. The heart failure may be, in certain embodiments, congestive heart failure, which is, in more specific embodiments, with preserved ejection fraction or without preserved ejection fraction. Congenital causes of muscle wasting include multiple sclerosis, spinal muscular atrophy; muscular dystrophies, for example Duchenne, Myotonic and Becker; mitochondrial myopathies, for example Myoclonic Epilepsy with Ragged Red Fibers (MERRF), Mitochondrial Encephalomyopathy, Lactic acidosis, and Stroke-like episodes (MELAS), Maternally Inherited Diabetes and Deafness (MIDD), Leber's Hereditary Optic Neuropathy (LHON), chronic progressive external ophthalmoplegia (CPEO), Leigh Disease, Kearns-Sayre Syndrome (KSS), Friedreich's Ataxia (FRDA), Co-Enzyme Q10 (CoQ10) deficiency, Complex I Deficiency, Complex II Deficiency, Complex III Deficiency, Complex IV Deficiency, and Complex V Deficiency); glycogen storage diseases of muscle, for example Pompe's, Andersen's and Cori's diseases; and myoglobinurias, for example McArdle, Tarui, and DiMauro diseases. In other embodiments, the muscle wasting, loss of muscle mass, or loss of muscle strength is due to dermatomyositis; familial periodic paralysis; or polymyositis, inclusion body myositis, or other inflammatory myopathies. In some embodiments, the treated disease is cachexia, for example due to multiple sclerosis, COPD, AIDS, heart failure, tuberculosis, familial amyloid polyneuropathy, mercury poisoning (acrodynia), or cancer. In other embodiments, the treated disease is sarcopenia. Alternatively or in addition, the muscle wasting, loss of muscle mass, or loss of muscle strength is mediated by inflammation. In still other embodiments, the loss of muscle mass occurs in a young person and has no apparent cause.

In another embodiment is provided use of ASC for the manufacture of a medicament identified for treatment of a muscle wasting disorder, non-limiting examples of which are muscular dystrophies. In another embodiment is provided use of ASC for the manufacture of a medicament identified for treatment of muscle wasting syndrome or muscle loss. In another embodiment is provided use of ASC for the manufacture of a medicament identified for prevention of muscle wasting syndrome and muscle loss. In another embodiment is provided use of ASC for the manufacture of a medicament identified for inhibiting muscle wasting syndrome or muscle loss.

In still another embodiment is provided an article of manufacture, comprising (a) a packaging material, wherein the packaging material comprises a label for use in treatment, prevention, or inhibition of a muscle wasting disorder, muscle wasting syndrome, or muscle loss; and (b) a pharmaceutical composition comprising ASC. In other embodiments, a pharmaceutical agent is contained within the packaging material, and the pharmaceutical agent is effective for treatment, prevention, or inhibition of muscle wasting syndrome and muscle loss; and the packaging material comprises a label which indicates that the pharmaceutical agent can be used for the aforementioned use(s). In some embodiments, the pharmaceutical composition is frozen. In other embodiments, the label indicates use in treatment of muscle wasting syndrome or muscle loss. In still other embodiments, the label indicates use in preventing muscle wasting syndrome or muscle loss. In still other embodiments, the label indicates use in inhibiting muscle wasting syndrome or muscle loss.

"Muscle wasting syndrome" is generally defined as loss of muscle mass. In some cases, the muscle wasting is not attributable to inactivity. Alternatively or in addition, the muscle wasting is rapid enough to be noticeable by a physician or veterinarian following the subject.

"Sarcopenia" is generally defined as loss of weight and muscle mass that occurs with advancing age. In more specific embodiments, the loss of skeletal muscle mass is at least 0.5% per year, or in more severe cases more than 1% loss per year. Alternatively or in addition, the loss of muscle mass has no apparent cause, other than advancing age. In still other embodiments, sarcopenia is considered to be present when sarcopenia when two criteria are fulfilled: (1) a low muscle mass and (2) a low gait speed (e.g. below 0.8 meters/second). Normal muscle mass is defined using data derived from young subjects aged 18-39 years from the Third NHANES population, and the requirement for a diagnosis of sarcopenia is the presence of a muscle mass ≥2 standard deviations below the mean of this reference population. In still other embodiments, (1) low muscle mass, (2) low muscle strength, and/or (3) low gait speed must all be present.

"Cachexia" is generally defined as severe, unintentional loss of lean body mass. In some cases, increasing caloric intake fails to reverse the loss of mass. In more specific embodiments, cachexia is considered to be present when all three of following criteria are met: (1) the presence of a chronic disease; (2) loss of body weight of at least 5% within the previous 12 months or less; and (3) the presence of at least three of the following: reduced muscle strength, fatigue, anorexia, a low fat-free mass index, abnormal biochemistry, inflammation, anemia, and low albumin levels. In certain cases, non-edematous weight loss is measured. In other cases, the fat-free mass index is measured. Cachexia can result from most or all of the causative disorders mentioned here.

In certain embodiments, the muscle wasting syndrome is acute muscle wasting syndrome (e.g. muscle wasting syndrome due to acute causes, such as burns and sepsis. In other embodiments, the muscle wasting syndrome is chronic muscle wasting syndrome, e.g. muscle wasting syndrome due to one of the chronic causes enumerated herein.

"Myopenia" as used herein indicates the presence of clinically relevant muscle wasting syndrome due to any illness and at any age.

Muscular dystrophies can be defined as inherited myogenic disorders characterised by progressive muscle wasting and weakness of variable distribution and severity (The Lancet Volume 359, No. 9307, p 687-695, 23 Feb. 2002). "Muscular dystrophy" (or "MD") as used herein refers to a muscle disease associated with one or more mutations in dystrophin (DMD; Uniprot Accession No. P11532, as accessed on Dec. 15, 2015) or genes that regulate dystrophin expression. Non-limiting examples of MD include Duchenne muscular dystrophy, Becker muscular dystrophy, myotonic muscular dystrophy, congenital muscular dystrophy, Emery-Dreifuss muscular dystrophy, facioscapulohumeral muscular dystrophy, limb-girdle muscular dystrophy, distal muscular dystrophy, DMD-associated dilated cardiomyopathy (DCM), and oculopharyngeal muscular dystrophy.

Methods for measuring muscle mass are well known in the art, and include, for example, Dual-energy X-ray absorptiometry (DEXA), currently considered the gold standard, bioelectrical impedance, computed tomography, magnetic resonance imaging, urinary excretion of creatinine, anthropometric assessments, and neutron activation assessments.

Methods for determining the effect of therapeutic modalities on muscle wasting syndrome and muscle loss in animal models and human subjects are well known in the art, and are described, for example in Baracos V et al, 2013, Doehner W et al, 2014, Zembroń-Łacny A et al 2014, and the references cited therein.

Methods for Preparing ASC

ASC can be propagated, in some embodiments, by using two-dimensional ("2D") culturing conditions, three-dimensional ("3D") culturing conditions, or a combination thereof. Conditions for propagating ASC in 2D and 3D culture are further described hereinbelow and in the Examples section which follows. These steps may be freely combined with any of the other described embodiments for culturing methods, characteristics of the cells, or therapeutic parameters, each of which is considered a separate embodiment.

As mentioned, in some embodiments, the cells have been propagated under 2D culturing conditions. The terms "2D culture" and "2D culturing conditions" refer to a culture in which the cells are exposed to conditions that are compatible with cell growth and allow the cells to grow in a monolayer, which is referred to as a "two-dimensional culture apparatus". Such apparatuses will typically have flat growth surfaces, in some embodiments comprising an adherent material, which may be flat or curved. Non-limiting examples of apparatuses for 2D culture are cell culture dishes and plates. Included in this definition are multi-layer trays, such as Cell Factory™, manufactured by Nunc™, provided that each layer supports monolayer culture. It will be appreciated that even in 2D apparatuses, cells can grow over one another when allowed to become over-confluent. This does not affect the classification of the apparatus as "two-dimensional".

In other embodiments, the cells have been propagated under 3D culturing conditions. The terms "3D culture" and "3D culturing conditions" refer to a culture in which the cells are exposed to conditions that are compatible with cell growth and allow the cells to grow in a 3D orientation relative to one another. The term "three-dimensional [or 3D] culture apparatus" refers to an apparatus for culturing cells under conditions that are compatible with cell growth and allow the cells to grow in a 3D orientation relative to one another. Such apparatuses will typically have a 3D growth surface, in some embodiments comprising an adherent material. Certain, non-limiting embodiments of 3D culturing conditions suitable for expansion of ASC are described in PCT Application Publ. No. WO/2007/108003, which is fully incorporated herein by reference in its entirety.

In various embodiments, an "adherent material" refers to a material that is synthetic, or in other embodiments naturally occurring, or in other embodiments a combination thereof. In certain embodiments, the material is non-cytotoxic (or, in other embodiments, is biologically compatible). Alternatively or in addition, the material is fibrous, which may be, in more specific embodiments, a woven fibrous matrix, a non-woven fibrous matrix, or either. In still other embodiments, the material exhibits a chemical structure that enables cell adhesion, for example charged surface-exposed moieties. Non-limiting examples of adherent materials which may be used in accordance with this aspect include a polyester, a polypropylene, a polyalkylene, a poly fluoro-chloro-ethylene, a polyvinyl chloride, a polystyrene, a polysulfone, a cellulose acetate, a glass fiber, a ceramic particle, a poly-L-lactic acid, and an inert metal fiber. Non-limiting examples of synthetic adherent materials include polyesters, polypropylenes, polyalkylenes, polyfluorochloroethylenes, polyvinyl chlorides, polystyrenes, polysulfones, cellulose acetates, and poly-L-lactic acids, glass fibers, ceramic particles, and an inert metal fiber, or, in more specific embodiments, polyesters, polypropylenes, polyalkylenes, polyfluorochloroethylenes, polyvinyl chlorides, polystyrenes, polysulfones, cellulose acetates, and poly-L-lactic acids. Other embodiments include Matrigel™, an extra-cellular matrix component (e.g., Fibronectin, Chondronectin, Laminin), and a collagen. In more particular embodiments, the material may be selected from a polyester and a polypropylene. Non-limiting examples of synthetic adherent materials include polyesters, polypropylenes, polyalkylenes, polyfluorochloroethylenes, polyvinyl chlorides, polystyrenes, polysulfones, cellulose acetates, and poly-L-lactic acids, glass fibers, ceramic particles, and an inert metal fiber, or, in more specific embodiments, polyesters, polypropylenes, polyalkylenes, polyfluorochloroethylenes, polyvinyl chlorides, polystyrenes, polysulfones, cellulose acetates, and poly-L-lactic acids.

Alternatively or in addition, the described ASC have been incubated in a 2D adherent-cell culture apparatus, prior to the step of 3D culturing. In some embodiments, cells (which have been extracted, in some embodiments, from placenta, from adipose tissue, etc.) are then subjected to prior step of incubation in a 2D adherent-cell culture apparatus, followed by the described 3D culturing steps. This step may be freely combined with any of the other described embodiments for culturing methods, characteristics of the cells, or therapeutic parameters, each of which is considered a separate embodiment.

In other embodiments, the length of 3D culturing is at least 4 days; between 4-12 days; in other embodiments between 4-11 days; in other embodiments between 4-10 days; in other embodiments between 4-9 days; in other embodiments between 5-9 days; in other embodiments between 5-8 days; in other embodiments between 6-8 days; or in other embodiments between 5-7 days.

According to other embodiments, the described 3D culturing is performed for at least 4 doublings, at least 5 doublings, at least 6 doublings, at least 7 doublings, at least 8 doublings, at least 9 doublings, or at least 10 doublings. In certain embodiments, cells are passaged when the culture reaches about 70-90% confluence, typically after 3-5 days (e.g., 1-3 doublings).

In certain embodiments, 3D culturing is performed in a 3D bioreactor. In some embodiments, the 3D bioreactor comprises a container for holding medium and a 3-dimensional attachment (carrier) substrate disposed therein; and a control apparatus, for controlling pH, temperature, and oxygen levels, and optionally other parameters. Alternatively or in addition, the bioreactor contains ports for the inflow and outflow of fresh medium and gases.

Examples of bioreactors include, but are not limited to, a continuous stirred tank bioreactor, a CelliGen Plus® bioreactor system (New Brunswick Scientific (NBS) and a BIO-FLO 310 bioreactor system (New Brunswick Scientific (NBS).

As provided herein, a 3D bioreactor is capable, in certain embodiments, of 3D expansion of ASC under controlled conditions (e.g. pH, temperature and oxygen levels) and with growth medium perfusion, which in some embodiments is constant perfusion and in other embodiments is adjusted in order to maintain target levels of glucose or other components. Non-limiting embodiments of target glucose concentrations are between 400-700 mg\liter, between 450-650 mg\liter, between 475-625 mg\liter, between 500-600 mg\liter, or between 525-575 mg\liter. Alternatively or in addition, the cell cultures can be directly monitored for concentrations of lactate, glutamine, glutamate and ammonium. The glucose consumption rate and the lactate formation rate of the adherent cells enable, in some embodiments, estimation of the cellular growth rate and determination of the optimal harvest time.

In some embodiments, for example where conditioned medium is being harvested, a continuous stirred tank bioreactor is used, where a culture medium is continuously fed into the bioreactor and a product is continuously drawn out, to maintain a time-constant steady state within the reactor. A stirred tank bioreactor with a fibrous bed basket is available for example from New Brunswick Scientific Co., Edison, N.J.). Additional bioreactors that may be used, in some embodiments, are stationary-bed bioreactors; and air-lift bioreactors, where air is typically fed into the bottom of a central draught tube flowing up while forming bubbles, and disengaging exhaust gas at the top of the column. Additional possibilities are cell-seeding perfusion bioreactors with polyactive foams [as described in Wendt, D. et al., Biotechnol Bioeng 84: 205-214, (2003)] and radial-flow perfusion bioreactors containing tubular poly-L-lactic acid (PLLA) porous scaffolds [as described in Kitagawa et al., Biotechnology and Bioengineering 93(5): 947-954 (2006). Other bioreactors which can be used are described in U.S. Pat. Nos. 6,277,151; 6,197,575; 6,139,578; 6,132,463; 5,902,741; and 5,629,186, which are fully incorporated herein by reference.

Another exemplary bioreactor, the Celligen 310 Bioreactor, is depicted in FIG. 1. A Fibrous-Bed Basket (16) is loaded with polyester disks (10). In some embodiments, the vessel is filled with deionized water or isotonic buffer via an external port (1 [this port may also be used, in other embodiments, for cell harvesting]) and then optionally autoclaved. In other embodiments, following sterilization, the liquid is replaced with growth medium, which saturates the disk bed as depicted in (9). In still further embodiments, temperature, pH, dissolved oxygen concentration, etc., are set prior to inoculation. In yet further embodiments, a slow stirring initial rate is used to promote cell attachment, then agitation is increased. Alternatively or addition, perfusion is initiated by adding fresh medium via an external port (2). If desired, metabolic products may be harvested from the cell-free medium above the basket (8). In some embodiments, rotation of the impeller creates negative pressure in the draft-tube (18), which pulls cell-free effluent from a reservoir (15) through the draft tube, then through an impeller port (19), thus causing medium to circulate (12) uniformly in a continuous loop. In still further embodiments, adjustment of a tube (6) controls the liquid level; an external opening (4) of this tube is used in some embodiments for harvesting. In other embodiments, a ring sparger (not visible), is located inside the impeller aeration chamber (11), for oxygenating the medium flowing through the impeller, via gases added from an external port (3), which may be kept inside a housing (5), and a sparger line (7). Alternatively or in addition, sparged gas confined to the remote chamber is absorbed by the nutrient medium, which washes over the immobilized cells. In still other embodiments, a water jacket (17) is present, with ports for moving the jacket water in (13) and out (14).

In certain embodiments, a perfused bioreactor is used, wherein the perfusion chamber contains carriers. The carriers may be, in more specific embodiments, selected from macrocarriers, microcarriers, or either. Non-limiting examples of microcarriers that are available commercially include alginate-based (GEM, Global Cell Solutions), dextran-based (Cytodex, GE Healthcare), collagen-based (Cultispher, Percell), and polystyrene-based (SoloHill Engineering) microcarriers. In certain embodiments, the microcarriers are packed inside the perfused bioreactor.

In some embodiments, the carriers in the perfused bioreactor are packed, for example forming a packed bed, which is submerged in a nutrient medium. Alternatively or in addition, the carriers may comprise an adherent material. In other embodiments, the surface of the carriers comprises an adherent material, or the surface of the carriers is adherent. In various embodiments in this context, "an adherent material" refers to a material that is synthetic, or in other embodiments naturally occurring, or in other embodiments a combination thereof. In certain embodiments, the material is non-cytotoxic (or, in other embodiments, is biologically compatible). Alternatively or in addition, the carriers comprise a fibrous material, optionally an adherent, fibrous material, which may be, in more specific embodiments, a woven fibrous matrix, a non-woven fibrous matrix, or either. Non-limiting examples of fibrous carriers are New Brunswick Scientific Fibracel® carriers, available commercially from of Eppendorf AG, Germany, and made of polyester and polypropylene; and BioNOC II carriers, available commercially from CESCO BioProducts (Atlanta, Ga.) and made of PET (polyethylene terephthalate). In still other embodiments, the material exhibits a chemical structure such as charged surface exposed groups, which allows cell adhesion. Non-limiting examples of adherent materials which may be used in accordance with this aspect include a polyester, a polypropylene, a polyalkylene, a polyfluorochloroethylene, a polyvinyl chloride, a polystyrene, a polysulfone, a cellulose acetate, a glass fiber, a ceramic particle, a poly-L-lactic acid, and an inert metal fiber. Non-limiting examples of synthetic adherent materials include polyesters, polypropylenes, polyalkylenes, polyfluorochloroethylenes, polyvinyl chlorides, polystyrenes, polysulfones, cellulose acetates, and poly-L-lactic acids, glass fibers, ceramic particles, and an inert metal fiber, or, in more specific embodiments, polyesters, polypropylenes, polyalkylenes, polyfluorochloroethylenes, polyvinyl chlorides, polystyrenes, polysulfones, cellulose acetates, and poly-L-lactic acids. Other embodiments include Matrigel™, an extra-cellular matrix component (e.g., Fibronectin, Chondronectin, Laminin), and a collagen. In more particular embodiments, the material may be selected from a polyester and a polypropylene. In certain embodiments, the referred-to fibrous matrix comprises a polyester, a polypropylene, a polyalkylene, a polyfluorochloroethylene, a polyvinyl chloride, a polystyrene, or a polysulfone. In more particular embodiments, the fibrous matrix is selected from a polyester and a polypropylene.

In other embodiments, cells are produced using a packed-bed spinner flask. In more specific embodiments, the packed bed may comprise a spinner flask and a magnetic stirrer. The spinner flask may be fitted, in some embodiments, with a packed bed apparatus, which may be, in more specific embodiments, a fibrous matrix; a non-woven fibrous matrix; non-woven fibrous matrix comprising polyester; or a non-woven fibrous matrix comprising at least about 50% polyester. In more specific embodiments, the matrix may be similar to the Celligen™ Plug Flow bioreactor which is, in certain embodiments, packed with Fibra-cel® (or, in other embodiments, other carriers). The spinner is, in certain embodiments, batch fed (or in other alternative embodiments fed by perfusion), fitted with one or more sterilizing filters, and placed in a tissue culture incubator. In further embodiments, cells are seeded onto the scaffold by suspending them in medium and introducing the medium to the apparatus. In still further embodiments, the agitation speed is gradually increased, for example by starting at 40 RPM for 4 hours, then gradually increasing the speed to 120 RPM. In certain embodiments, the glucose level of the medium may be tested periodically (i.e. daily), and the perfusion speed adjusted maintain an acceptable glucose concentration, which is, in certain embodiments, between 400-700 mg\liter, between 450-650 mg\liter, between 475-625 mg\liter, between 500-600 mg\liter, or between 525-575 mg\liter. In yet other embodiments, at the end of the culture process, carriers are removed from the packed bed, washed with isotonic buffer, and processed or removed from the carriers by agitation and/or enzymatic digestion.

In certain embodiments, the bioreactor is seeded at a concentration of between 10,000-2,000,000 cells/ml of medium, in other embodiments 20,000-2,000,000 cells/ml, in other embodiments 30,000-1,500,000 cells/ml, in other embodiments 40,000-1,400,000 cells/ml, in other embodiments 50,000-1,300,000 cells/ml, in other embodiments 60,000-1,200,000 cells/ml, in other embodiments 70,000-1,100,000 cells/ml, in other embodiments 80,000-1,000,000 cells/ml, in other embodiments 80,000-900,000 cells/ml, in other embodiments 80,000-800,000 cells/ml, in other embodiments 80,000-700,000 cells/ml, in other embodiments 80,000-600,000 cells/nil, in other embodiments 80,000-500,000 cells/ml, in other embodiments 80,000-400,000 cells/ml, in other embodiments 90,000-300,000 cells/ml, in other embodiments 90,000-250,000 cells/ml, in other embodiments 90,000-200,000 cells/ml, in other embodiments 100,000-200,000 cells/ml, in other embodiments 110,000-1,900,000 cells/ml, in other embodiments 120,000-1,800,000 cells/ml, in other embodiments 130,000-1,700,000 cells/ml, in other embodiments 140,000-1,600,000 cells/ml.

In still other embodiments, between $1-20\times10^6$ cells per gram (gr) of carrier (substrate) are seeded, or in other embodiments $1.5-20\times10^6$ cells/gr carrier, or in other embodiments $1.5-18\times10^6$ cells/gr carrier, or in other embodiments $1.8-18\times10^6$ cells/gr carrier, or in other embodiments $2-18\times10^6$ cells/gr carrier, or in other embodiments $3-18\times10^6$ cells/gr carrier, or in other embodiments $2.5-15\times10^6$ cells/gr carrier, or in other embodiments $3-15\times10^6$ cells/gr carrier, or in other embodiments $3-14\times10^6$ cells/gr carrier, or in other embodiments $3-12\times10^6$ cells/gr carrier, or in other embodiments $3.5-12\times10^6$ cells/gr carrier, or in other embodiments $3-10\times10^6$ cells/gr carrier, or in other embodiments $3-9\times10^6$ cells/gr carrier, or in other embodiments $4-9\times10^6$ cells/gr carrier, or in other embodiments $4-8\times10^6$ cells/gr carrier, or in other embodiments $4-7\times10^6$ cells/gr carrier, or in other embodiments $4.5-6.5\times10^6$ cells/gr carrier.

In certain embodiments, the described method further comprises the subsequent step (following the described 3D incubation) of harvesting the ASC by removing the ASC from the 3D culture apparatus. In certain embodiments, the harvest from the bioreactor is performed when at least about 10%, at least 12%, at least 14%, at least 16%, at least 18%, at least 20%, at least 22%, at least 24%, at least 26%, at least 28%, or at least 30% of the cells are in the S and G2/M phases (collectively), as can be assayed by various methods known in the art, for example FACS detection. Typically, in the case of FACS, the percentage of cells in S and G2/M phase is expressed as the percentage of the live cells, after gating for live cells, for example using a forward scatter/side scatter gate. Those skilled in the art will appreciate that the percentage of cells in these phases correlates with the percentage of proliferating cells. In some cases, allowing the cells to remain in the bioreactor significantly past their logarithmic growth phase causes a reduction in the number of cells that are proliferating.

In other embodiments, the described incubation of ASC comprises microcarriers, which may, in certain embodiments, be inside a bioreactor. Microcarriers are well known to those skilled in the art, and are described, for example in U.S. Pat. Nos. 8,828,720, 7,531,334, 5,006,467, which are incorporated herein by reference. Microcarriers are also commercially available, for example as Cytodex™ (available from Pharmacia Fine Chemicals, Inc.,) Superbeads (commercially available from Flow Labs, Inc.,), and as DE-52 and DE-53 (commercially available from Whatman, Inc.). In certain embodiments, the ASC may be incubated in a 2D apparatus, for example tissue culture plates or dishes, prior to incubation in microcarriers. In other embodiments, the ASC are not incubated in a 2D apparatus prior to incubation in microcarriers. In certain embodiments, the microcarriers are packed inside a bioreactor.

Figure 12A:
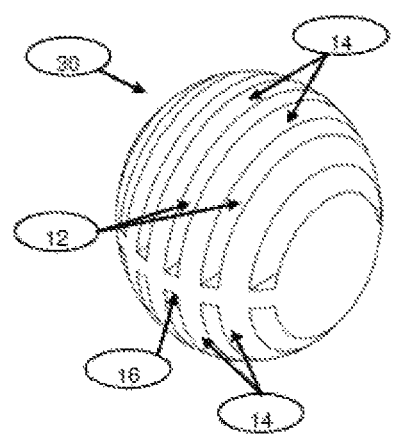
FIG. 12A is a perspective view of a carrier (or "3D body"), according to an exemplary embodiment.
Figure 12B:
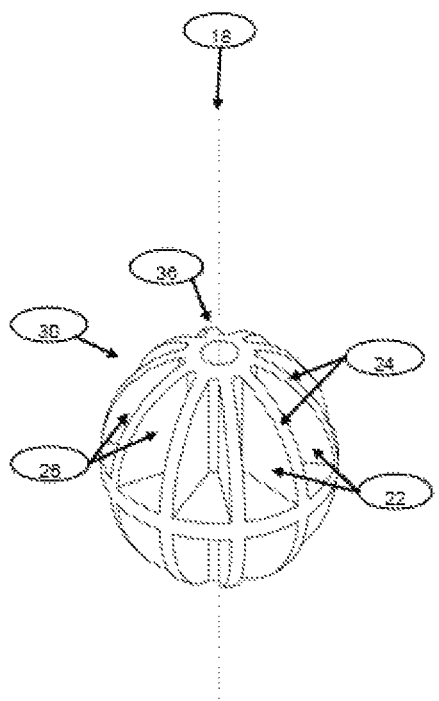
FIG. 12B is a perspective view of a carrier, according to another exemplary embodiment.

In some embodiments, with reference to FIGS. 12A-B, and as described in WO/2014/037862, published on Mar. 13, 2014, which is incorporated herein by reference in its entirety, channel-containing carriers 30 are used for proliferation, or, in other embodiments, induction, of ASC. In various embodiments, the carriers may be used following a 2D incubation (e.g. on culture plates or dishes), or without a prior 2D incubation. In other embodiments, incubation on the carriers may be followed by incubation on a 3D substrate in a bioreactor, which may be, for example, a packed-bed substrate or microcarriers; or incubation on the carriers may not be followed by incubation on a 3D substrate. In still other embodiments, incubation on the carriers is followed by induction on a 3D substrate in a bioreactor, which may be, for example, a packed-bed substrate or microcarriers. In yet other embodiments, incubation on the carriers is followed by incubation on a 3D substrate in a bioreactor, which includes in the latter portion of the incubation, induction of the cells.

Figure 12C:
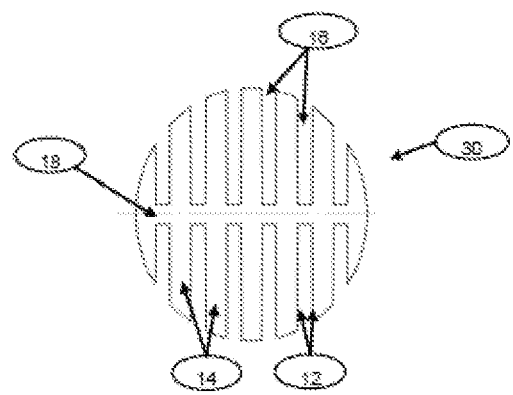
FIG. 12C is a cross-sectional view of a carrier, according to an exemplary embodiment.

With reference to FIG. 12A, carriers 30 can include multiple two-dimensional (2D) surfaces 12 extending from an exterior of carrier 30 towards an interior of carrier 30. As shown, the surfaces are formed by a group of ribs 14 that are spaced apart to form openings 16, which may be sized to allow flow of cells and culture medium (not shown) during use. With reference to FIG. 12C, carrier 30 can also include multiple 2D surfaces 12 extending from a central carrier axis 18 of carrier 30 and extending generally perpendicular to ribs 14 that are spaced apart to form openings 16, creating multiple 2D surfaces 12. In more specific embodiments, the central carrier axis 18 of carrier 30 is a plane that bisects the sphere, and openings 16 extend from the surface of the carrier to the proximal surface of the plane. In some embodiments, carriers 30 are "3D bodies" as described in WO/2014/037862; the contents of which relating to 3D bodies are incorporated herein by reference.

As mentioned, carrier 30 may have a variety of shapes, including but not limited to spherical, cylindrical, cubical, hyperrectangular, ellipsoid, and polyhedral and/or irregular polyhedral shapes. In some embodiments, the diameter of the minimal bounding sphere (e.g. the diameter of the carrier, in the case of a spherical shape) of carrier 30 can range from 1-50 mm. In other embodiments, the outer largest dimension can range from 2-20 mm, from 3-15 mm, or from 4-10 mm. In other embodiments, the generic chord length of carriers 30 ranges from 0.5-25 mm, from 1-10 mm, from 1.5-7.5 mm, from 2-5 mm, or from 2.5-4 mm. As known to those skilled in the art, generic chord length is described inter alia in Li et al, Determination of non-spherical particle size distribution from chord length measurements. Part 1: Theoretical analysis. Chemical Engineering Science 60(12): 3251-3265, 2005)

With reference to FIGS. 12A and 12C, depending upon the overall size of carrier 30, ribs 14 and openings 16 can be variously sized. For example, ribs 14 can range in thickness from 0.1-2 mm or from 0.2 mm-1 mm. In particular, ribs 14 can be 0.4-0.6 mm, 0.5-0.7 mm, or 0.6-0.8 mm in thickness. Openings 16 can range in width from 0.01-1 mm or from 0.1-0.5 mm. In particular, openings 16 can be 0.25-0.35 mm, 0.35-0.45 mm, or 0.45-0.55 mm in width.

In preferred embodiments, the carriers provide 2D surfaces for attachment and monolayer growth over at least a majority of or all of the surface area of the multiple 2D surfaces 12, 22. Alternatively or in addition, the carriers have a surface area to volume ratio is between 3-1000 $cm^2/cm^3$, between 3-500 $cm^2/cm^3$, between 3-300 $cm^2/cm^3$, between 3-200 $cm^2/cm^3$, between 3-100 $cm^2/cm^3$, between 3-50 $cm^2/cm^3$, between 3-30 $cm^2/cm^3$, between 5-20 $cm^2/cm^3$, or between 10-15 $cm^2/cm^3$.

As shown in FIGS. 12A-B, carriers 30 may be substantially spherical and have a diameter that forms the carriers' largest dimension. In some embodiments, a diameter of carrier 30 can range from 1-50 mm. In other embodiments, the diameter can range from 2-20 mm, 3-15, mm, or 4-10 mm. Depending upon the overall size of carrier 30, ribs 24 and openings 26 can be variously sized. For example, ribs 24 can range in thickness from 0.1-2 mm or from 0.2-1 mm. In particular, ribs 24 can be 0.45-0.55 mm, 0.55-0.65 mm, or 0.65-0.75 mm in thickness. As shown in FIG. 12B, a minimum width of openings 26 can range from 0.01-1 mm, from 0.05-0.8 mm, or from 0.1-0.5 mm. Specifically, the minimum width of openings 26 can be 0.25-0.35 mm, 0.3.5-0.45 mm, or 0.45-0.55 mm. In other embodiments, the largest cross-sectional dimension of opening 36 can range from 0.1-5 mm, from 0.2-3 mm, or from 0.5-2 mm. More particularly, opening 36 can have a largest cross-sectional dimension of 0.7.5-0.85 mm, 0.95-1.05 mm, or 1.15-0.25 mm.

In the embodiment shown in FIG. 12A, ribs 14 are substantially flat and extend parallel to one another. In other embodiments, the ribs are in other configurations. For example, FIG. 12B illustrates carrier 30 having multiple two-dimensional surfaces 22 formed by ribs 24 in a different configuration. In particular, ribs 24 are shaped to form openings 26 that are spaced around the circumference of carrier 30, whereby openings 26 can be generally wedge shaped. Ribs 24 can extend generally radially from a central carrier axis 18 of carrier 30 to a peripheral surface of carrier 30. Carrier 30 can also include one or more lateral planes extending from the central carrier axis 18 of carrier 30 and extending generally perpendicular to ribs 24, as depicted in FIG. 12C, which is a cross-sectional view of certain embodiments of the carrier 30 of FIG. 12A. Further, carrier 30 includes an opening 36 extending through the carrier's center and forming additional surfaces 32, which can support monolayer growth of eukaryotic cells.

In still other embodiments, the material forming the multiple 2D surfaces comprises at least one polymer. In more specific embodiments, the polymer is selected from a polyamide, a polycarbonate, a polysulfone, a polyester, a polyacetal, and polyvinyl chloride.

The material used to produce the described carriers can include, in various embodiments, metals (e.g. titanium), metal oxides (e.g., titanium oxide films), glass, borosilicate, carbon fibers, ceramics, biodegradable materials (e.g. collagen, gelatin, PEG, hydrogels), and or polymers. Suitable polymers may include polyamides, such as GRILAMID® TR 55 (EMS-Grivory, Sumter, S.C.); polycarbonates such as LEXAN® (Sabic, Pittsfield, Mass.) and Macrolon® (Bayer); polysulfones such as RADEL® PPSU (Solvay) and UDEL® PSU (Solvay); polyesters such as TRITAN® (Polyone) and PBT® HX312C; polyacetals such as CELON® (Ticana), and polyvinyl chloride. In certain embodiments, the described carriers are composed of a non-porous material, or, if pores are present, they are no larger than 20 microns, in other embodiments 10 microns, in other embodiments 5 microns, in other embodiments 3 microns, in other embodiments 2 microns, or in other embodiments 1 micron.

In more specific embodiments, cell-culture carriers are formed of injection-molded surface treatment of LEXAN® or GRILAMID®, with a smooth surface texture, using growth medium proteins and/or polylysine on LEXAN® or GRILAMID® carriers; cell-culture carriers formed of injection-molded GRILAMID® with a rough surface that was preincubated with growth medium proteins. In other embodiments, untreated LEXAN® or GRILAMID® surfaces are utilized.

In other embodiments, at least part of the carriers may be formed using a polystyrene polymer. The polystyrene may be further modified using corona discharge, gas-plasma (roller bottles and culture tubes), or other similar processes. These processes can generate highly energetic oxygen ions which graft onto the surface polystyrene chains so that the surface becomes hydrophilic and negatively charged when medium is added. Furthermore, any of the carriers may be produced at least in part from combinations of materials. Materials of the carriers can be further coated or treated to support cell attachment. Such coating and/or pretreatment may include use of collagen I, collagen IV, gelatin, poly-d-lysine, fibronectin, laminin, amine, and carboxyl.

In various embodiments, the described carriers are coated with one or more coatings.

Suitable coatings may, in some embodiments, be selected to control cell attachment or parameters of cell biology. Suitable coatings may include, for example, peptides, proteins, carbohydrates, nucleic acid, lipids, polysaccharides, glycosaminoglycans, proteoglycans, hormones, extracellular matrix molecules, cell adhesion molecules, natural polymers, enzymes, antibodies, antigens, polynucleotides, growth factors, synthetic polymers, polylysine, drugs and/or other molecules or combinations or fragments of these.

Furthermore, in various embodiments, the surfaces of the carriers described herein may be treated or otherwise altered to control cell attachment and or other biologic properties. Options for treating the surfaces include chemical treatment, plasma treatment, and/or corona treatment. Further, in various embodiments, the materials may be treated to introduce functional groups into or onto the material, including groups containing hydrocarbons, oxygen, and/or nitrogen. In addition, in various embodiments, the material may be produced or altered to have a texture to facilitate settling of cells or control other cell properties. For example, in some embodiments, the materials used to produce the cell-culture carriers have a roughness on a nanometer or micrometer scale that facilitates settling of cells and/or controls other cell properties.

Harvesting

In still other embodiments, the harvest utilizes vibration, for example as described in PCT International Application Publ. No. WO 2012/140519, which is incorporated herein by reference. This step may be freely combined with any of the other described embodiments for culturing methods, characteristics of the cells, or therapeutic parameters, each of which is considered a separate embodiment. In certain embodiments, during harvesting, the cells are vibrated at 0.7-6 Hertz, or in other embodiments 1-3 Hertz, during, or in other embodiments during and after, treatment with protease plus a calcium chelator, non-limiting examples of which are trypsin, or another enzyme with similar activity, optionally in combination with another enzyme, non-limiting examples of which are Collagenase, Types I, II, III, and IV, with EDTA. Enzymes with similar activity to trypsin are well known in the art; non-limiting examples are a fungal trypsin-like protease, TrypLE™, and Collagenase, Types I, II, III, and IV, which are available commercially from Life Technologies. Enzymes with similar activity to collagenase are well known in the art; non-limiting examples are Dispase I and Dispase II, which are available commercially from Sigma-Aldrich. In more specific embodiments, the total duration of vibration during and/or after treatment with protease plus a calcium chelator is between 2-10 minutes, in other embodiments between 3-9 minutes, in other embodiments between 3-8 minutes, and in still other embodiments between 3-7 minutes. In still other embodiments, the cells are subjected to vibration at 0.7-6 Hertz, or in other embodiments 1-3 Hertz, during the wash step before the protease and calcium chelator are added.

Cells Subjected to Pro-Inflammatory Cytokines

In certain embodiments of the described methods, the composition of the medium is not varied during the course of the 3D culture. In other words, no attempt is made to intentionally vary the medium composition by adding or removing factors or adding fresh medium with a different composition than the previous medium. Reference to varying the composition of the medium does not include variations in medium composition that automatically occur as a result of prolonged culturing, for example due to the absorption of nutrients and the secretion of metabolites by the cells therein, as will be appreciated by those skilled in the art.

In other embodiments, the 3D culturing method used to prepare the cells comprises the steps of: (a) incubating ASC in a 3D culture apparatus in a first growth medium, wherein no inflammatory cytokines have been added to the first growth medium; and (b) subsequently incubating the ASC in a 3D culture apparatus in a second growth medium, wherein one or more pro-inflammatory cytokines have been added to the second growth medium. Those skilled in the art will appreciate, in light of the present disclosure, that the same 3D culture apparatus may be used for the incubations in the first and second growth medium by simply adding cytokines to the medium in the culture apparatus, or, in other embodiments, by removing the medium from the culture apparatus and replacing it with medium that contains cytokines. In other embodiments, a different 3D culture apparatus may be used for the incubation in the presence of cytokines, for example by moving (e.g. passaging) the cells to a different incubator, before adding the cytokine-containing medium. Those skilled in the art will appreciate, in light of the present disclosure, that the ASC to be used in the described methods may be extracted, in various embodiments, from the placenta, from adipose tissue, or from other sources, as described further herein.

Reference herein to one or more "pro-inflammatory" cytokines, or "inflammatory cytokines", which are used interchangeably, implies the presence of at least one cytokine that mediates an inflammatory response in a mammalian host, for example a human host. A non-limiting list of cytokines are Interferon-gamma (IFN-gamma or IFN-gamma; UniProt identifier P01579), IL-22 (UniProt identifier Q9GZX6), Tumor Necrosis Factor-alpha (TNF-alpha; UniProt identifier P01375), IFN-alpha, IFN-beta (UniProt identifier P01574), IL-1alpha (UniProt identifier P01583), IL-1beta (UniProt identifier P01584), IL-17 (UniProt identifier Q5QEX9), IL-23 (UniProt identifier Q9NPF7), IL-17A (UniProt identifier Q16552), IL-17F (UniProt identifier Q96PD4), IL-21 (UniProt identifier Q9HBE4), IL-13 (UniProt identifier P35225), IL-5 (UniProt identifier P05113), IL-4 (UniProt identifier P05112), IL-33 (UniProt identifier O95760), IL-1RL1 (UniProt identifier Q01638), TNF-Beta (UniProt identifier P01374), IL-11 (UniProt identifier P20809), IL-9 (UniProt identifier P15248), IL-2 (UniProt identifier P60568), IL-21 (UniProt identifier Q9HBE4), Tumor Necrosis Factor-Like Ligand (TL1A; a.k.a. TNF ligand superfamily member 15; UniProt identifier O95150), IL-12 (UniProt identifiers P29459 and P29460 for the alpha- and beta subunits, respectively), and IL-18 (UniProt identifier Q14116). Additional cytokines include (but are not limited to): Leukemia inhibitory factor (LIF; UniProt identifier P15018), oncostatin M (OSM; UniProt identifier P13725), ciliary neurotrophic factor (CNTF (UniProt identifier P26441), and IL-8 (UniProt identifier P10145). All Swissprot and UniProt entries were accessed on Jul. 24, 2014.

Except where indicated otherwise, reference to a cytokine or other protein is intended to include all isoforms of the protein. For example, IFN-alpha includes all the subtypes and isoforms thereof, such as but not limited to IFN-alpha 17, IFN-alpha 4, IFN-alpha 7, IFN-alpha 8, and IFN-alpha 110. Some representative UniProt identifiers for IFN-alpha are P01571, P05014, P01567, P32881, and P01566. Those skilled in the art will appreciate that, even in the case of human cells, the aforementioned cytokines need not be human cytokines, since many non-human (e.g. animal) cytokines are active on human cells. Similarly, the use of modified cytokines that have similar activity to the native forms falls within the scope of the described methods and compositions.

In certain embodiments, the cytokine present in the described medium, or in other embodiments at least one of the cytokines present, if more than one is present, is an inflammatory cytokine that affects innate immune responses. In further embodiments, the cytokine is one of, or in other embodiments more than one, of TNF-α, IL-1alpha, IL-12, IFN-α IFN-β, or IFN-γ.

In other embodiments, the cytokine, or in other embodiments at least one of the cytokines, if more than one is present, is an inflammatory cytokine that affects adaptive immune responses. In further embodiments, the cytokine is one of, or in other embodiments more than one, of IL-2, IL-4, IL-5, TGF-β, or IFN-γ.

In still other embodiments, the cytokine, or in other embodiments at least one of the cytokines, if more than one is present, is a Th1 cytokine. In further embodiments, the cytokine is one of, or in other embodiments more than one, of IFN-gamma, IL-22, TNF-alpha, IL-1alpha, or IL-1beta.

In still other embodiments, the cytokine, or in other embodiments at least one of the cytokines, if more than one is present, is a Th17 cytokine. In further embodiments, the cytokine is one of, or in other embodiments more than one, of IL-17, IL-23, IL-17A, IL-17F, IL-21, IL-22, TNF-alpha, or granulocyte macrophage colony stimulating factor (GM-CSF; UniProt identifier P04141).

In yet other embodiments, the cytokine, or in other embodiments at least one of the cytokines, if more than one is present, is selected from a Th1 cytokine and a Th17 cytokine.

In still other embodiments, the cytokine, or in other embodiments at least one of the cytokines, if more than one is present, is a Th2 cytokine. In further embodiments, the cytokine is one of, or in other embodiments more than one, of IL-13, IL-5, IL-4, IL-33, IL-1RL1, TNF-Alpha, and TNF-Beta. In other embodiments, the cytokine is one of, or in other embodiments more than one, of IL-13, IL-5, IL-33, IL-1RL1, TNF-Alpha, or TNF-Beta.

In yet other embodiments, the cytokine(s) is one of, or in other embodiments more than one, of IL-11 (maybe IL-9, IL-2, I think IL-21) Leukemia inhibitory factor (LIF), oncostatin M (OSM), ciliary neurotrophic factor (CNTF), granulocyte macrophage colony stimulating factor (GM-CSF), and IL-8. In further embodiments, the cytokine(s) is one or more of IL-11, LIF, OSM, CNTF, GM-CSF, or IL-8.

In other embodiments, the cytokine(s) is one of, or in other embodiments more than one, of: TNF-α, IL-1beta, or TL1A.

In yet other embodiments, the cytokine(s) is one of, or in other embodiments more than one, of IL-12, IL-18, TNF-α.

In more specific embodiments, one of the aforementioned cytokines is present in the medium in an amount of 0.1-10 ng/ml; 0.15-10 ng/ml; 0.2-10 ng/ml; 0.3-10 ng/ml; 0.4-10 ng/ml; 0.5-10 ng/ml; 0.7-10 ng/ml; 1-10 ng/ml; 1.5-10 ng/ml; 2-10 ng/ml; 3-10 ng/ml; 4-10 ng/ml; 5-10 ng/ml; 0.1-5 ng/ml; 0.2-5 ng/ml; 0.3-5 ng/ml; 0.4-5 ng/ml; 0.5-5 ng/ml; 0.7-5 ng/ml; 1-5 ng/ml; 2-5 ng/ml; 0.1-3 ng/ml; 0.2-3 ng/ml; 0.3-3 ng/ml; 0.4-3 ng/ml; 0.5-3 ng/ml; 0.6-3 ng/ml; 0.8-3 ng/ml; 1-3 ng/ml; 1.5-3 ng/ml; 0.1-2 ng/ml; 0.2-2 ng/ml; 0.3-2 ng/ml; 0.4-2 ng/ml; 0.5-2 ng/ml; 0.6-2 ng/ml; 0.8-2 ng/ml; 1-2 ng/ml; 0.5-1.5 ng/ml; 0.6-1.5 ng/ml; 0.6-1.4 ng/ml; 0.7-1.3 ng/ml; 0.8-1.2 ng/ml; 0.1-0.8 ng/ml; 0.1-0.6 ng/ml; 0.1-0.5 ng/ml; 0.1-0.4 ng/ml; 0.2-1 ng/ml; 0.2-0.8 ng/ml; 0.2-0.6 ng/ml; 0.2-0.5 ng/ml; 0.2-0.4 ng/ml; 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; 2-4 ng/ml; 10-1000 ng/ml; 20-1000 ng/ml; 30-1000 ng/ml; 40-1000 ng/ml; 50-1000 ng/ml; 70-1000 ng/ml; 100-1000 ng/ml; 150-1000 ng/ml; 200-1000 ng/ml; 300-1000 ng/ml; 400-1000 ng/ml; 500-1000 ng/ml; 10-500 ng/ml; 20-500 ng/ml; 30-500 ng/ml; 40-500 ng/ml; 50-500 ng/ml; 70-500 ng/ml; 100-500 ng/ml; 200-500 ng/ml; 10-300 ng/ml; 20-300 ng/ml; 30-300 ng/ml; 40-300 ng/ml; 50-300 ng/ml; 60-300 ng/ml; 80-300 ng/ml; 100-300 ng/ml; 150-300 ng/ml; 10-200 ng/ml; 20-200 ng/ml; 30-200 ng/ml; 40-200 ng/ml; 50-200 ng/ml; 60-200 ng/ml; 80-200 ng/ml; 100-200 ng/ml; 50-150 ng/ml; 60-15 ng/ml; 60-14 ng/ml; 70-130 ng/ml; 80-120 ng/ml; 10-100 ng/ml; 10-80 ng/ml; 10-60 ng/ml; 10-50 ng/ml; 10-40 ng/ml; 20-100 ng/ml; 20-80 ng/ml; 20-60 ng/ml; 20-50 ng/ml; or 20-40 ng/ml. In still other embodiments, when more than one cytokines is present, each of them is present in an amount independently selected from the above amounts, which may be freely combined. In various other embodiments, the amounts of each of the proinflammatory cytokines present are each within one of the above ranges.

In certain embodiments, one or more of the cytokines is TNF-alpha. In more specific embodiments, the TNF-alpha may be the only cytokine present, or, in other embodiments, may be present together with 1, 2, 3, 4, 5, 6, 1-2, 1-3, 1-4, 1-5, or 1-6, or more than 6 added inflammatory cytokines, which may be, in certain embodiments, one of the aforementioned cytokines. In more specific embodiments, TNF-alpha is present in an amount of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml.

In some embodiments, TNF-alpha is present in the medium together with IFN-gamma. These two cytokines may be the only 2 added cytokines, or, in other embodiments, present with additional proinflammatory cytokines. In still other embodiments, IFN-gamma and TNF-alpha are each present in an amount independently selected from one of the aforementioned amounts or ranges. Each combination may be considered as a separate embodiment. In still other embodiments, the amounts of IFN-gamma and TNF-alpha are both within the range of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml.

As mentioned, in some embodiments, TNF-alpha is present together with one, or in other embodiments 2, 3, 4, 5, or more than 5, of the aforementioned cytokines. In still other embodiments, TNF-alpha and one, or in other embodiments more than one, of the additional cytokines is each present in an amount independently selected from one of the aforementioned amounts or ranges. Each combination may be considered as a separate embodiment. In still other embodiments, the amounts of TNF-alpha and the other cytokine(s) are both within the range of 1-100 ng/ml; 2-100 ng/ml; 3-100 ng/ml; 4-100 ng/ml; 5-100 ng/ml; 7-100 ng/ml;

10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml.

In certain embodiments, one or more of the cytokines is IFN-gamma. In more specific embodiments, the IFN-gamma may be the only cytokine present, or, in other embodiments, may be present together with 1, 2, 3, 4, 5, 6, 1-2, 1-3, 1-4, 1-5, or 1-6, or more than 6 added cytokines. In more specific embodiments, IFN-gamma is present in an amount of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml.

As mentioned, in some embodiments, IFN-gamma is present together with one of the aforementioned cytokines. These two cytokines may be the only 2 added cytokines, or, in other embodiments, present with additional proinflammatory cytokines. In still other embodiments, IFN-gamma and one, or in other embodiments more than one, of the additional cytokines is each present in an amount independently selected from one of the aforementioned amounts or ranges. Each combination may be considered as a separate embodiment. In still other embodiments, the amounts of IFN-gamma and the other cytokine(s) are both within the range of 1-100 ng/ml; 2-100 ng/ml; 3-100 ng/ml; 4-100 ng/ml; 5-100 ng/ml; 7-100 ng/ml; 10-100 ng/ml; 15-100 ng/ml; 20-100 ng/ml; 30-100 ng/ml; 40-100 ng/ml; 50-100 ng/ml; 1-50 ng/ml; 2-50 ng/ml; 3-50 ng/ml; 4-50 ng/ml; 5-50 ng/ml; 7-50 ng/ml; 10-50 ng/ml; 20-50 ng/ml; 1-30 ng/ml; 2-30 ng/ml; 3-30 ng/ml; 4-30 ng/ml; 5-30 ng/ml; 6-30 ng/ml; 8-30 ng/ml; 10-30 ng/ml; 15-30 ng/ml; 1-20 ng/ml; 2-20 ng/ml; 3-20 ng/ml; 4-20 ng/ml; 5-20 ng/ml; 6-20 ng/ml; 8-20 ng/ml; 10-20 ng/ml; 5-15 ng/ml; 6-15 ng/ml; 6-14 ng/ml; 7-13 ng/ml; 8-12 ng/ml; 9-11 ng/ml; 9.5-10.5 ng/ml; 1-10 ng/ml; 1-8 ng/ml; 1-6 ng/ml; 1-5 ng/ml; 1-4 ng/ml; 2-10 ng/ml; 2-8 ng/ml; 2-6 ng/ml; 2-5 ng/ml; or 2-4 ng/ml.

In other embodiments, the aforementioned step (a) (3D incubation in the absence of inflammatory cytokines) is performed for at least 3 days, at least 4 days, at least 5 days, at least 6 days, or at least 7 days. In other embodiments, step (a) is performed for between 3-4 days, 3-5 days, 3-6 days, 3-7 days, 4-5 days, 4-6 days, 4-7 days, 5-6 days, 5-7 days, or 6-7 days. In still other embodiments, step (a) is performed for at least 1 population doubling, at least 2 doublings, at least 3 doublings, at least 4 doublings, 1-2 doublings, 1-3 doublings, 1-4 doublings, 2-3 doublings, 2-4 doublings, or 3-4 doublings.

Alternatively or in addition, the aforementioned step (b) (3D incubation in the presence of inflammatory cytokines) is performed for between 6-48 hours, 8-48 hours, 10-48 hours, 12-48 hours, 14-48 hours, 16-48 hours, 20-48 hours, 6-36 hours, 8-36 hours, 10-36 hours, 12-36 hours, 14-36 hours, 16-36 hours, 20-36 hours, 24-36 hours, 28-36 hours, 6-24 hours, 8-24 hours, 10-24 hours, 12-24 hours, 14-24 hours, 16-24 hours, 20-24 hours, 8-18 hours, 10-18 hours, 12-18 hours, or 14-18 hours.

In still other embodiments, step (a) is performed for 3-7 days, and step (b) is performed for 12-48 hours; step (a) is performed for 3-6 days, and step (b) is performed for 12-48 hours; step (a) is performed for 4-7 days, and step (b) is performed for 12-48 hours; step (a) is performed for 4-6 days, and step (b) is performed for 12-48 hours; step (a) is performed for 3-7 days, and step (b) is performed for 12-36 hours; step (a) is performed for 3-6 days, and step (b) is performed for 12-36 hours; step (a) is performed for 4-7 days, and step (b) is performed for 12-36 hours; step (a) is performed for 4-6 days, and step (b) is performed for 12-36 hours; step (a) is performed for 3-7 days, and step (b) is performed for 16-36 hours; step (a) is performed for 3-6 days, and step (b) is performed for 16-36 hours; step (a) is performed for 4-7 days, and step (b) is performed for 16-36 hours; step (a) is performed for 4-6 days, and step (b) is performed for 16-36 hours; step (a) is performed for 3-7 days, and step (b) is performed for 16-36 hours; step (a) is performed for 3-6 days, and step (b) is performed for 16-36 hours; step (a) is performed for 4-7 days, and step (b) is performed for 16-36 hours; or step (a) is performed for 4-6 days, and step (b) is performed for 16-36 hours. In other embodiments, step (a) is performed for 3-7 days, and step (b) is performed for 12-24 hours; step (a) is performed for 3-6 days, and step (b) is performed for 12-24 hours; step (a) is performed for 4-7 days, and step (b) is performed for 12-24 hours; step (a) is performed for 4-6 days, and step (b) is performed for 12-24 hours; step (a) is performed for 3-7 days, and step (b) is performed for 12-24 hours; step (a) is performed for 3-6 days, and step (b) is performed for 12-24 hours; step (a) is performed for 4-7 days, and step (b) is performed for 12-24 hours; or step (a) is performed for 4-6 days, and step (b) is performed for 12-24 hours.

In certain embodiments, at least part of the aforementioned step (a) is performed in perfusion mode. In other embodiments, the majority of step (a) (the majority of the 3D culturing time in the absence of inflammatory cytokines) is performed in perfusion mode. In still other embodiments, all of step (a) is performed in perfusion mode. In other embodiments, at least part of step (a) is performed in batch mode.

Alternatively or in addition, at least part of step (b) is performed in batch mode. In other embodiments, the majority of step (b) (the majority of the 3D culturing time in the presence of inflammatory cytokines) is performed in batch mode. In still other embodiments, all of step (b) is performed in batch mode. In other embodiments, at least part of step (b) is performed in perfusion mode. In certain embodiments, the majority of step (a) is performed in perfusion mode, and the majority of step (b) is performed in batch mode.

In certain embodiments, the ASC, prior to their ex vivo exposure to cytokines, are placental-derived, adipose-derived, or bone marrow (BM)-derived ASC. Alternatively or in addition, the ASC are mesenchymal-like adherent stromal cells, which exhibit a marker pattern similar to "classical" MSC, but do not differentiate into osteocytes, under conditions where "classical" MSC would differentiate into osteocytes. In other embodiments, the cells exhibit a marker pattern similar to MSC, but do not differentiate into adipocytes, under conditions where MSC would differentiate into adipocytes. In still other embodiments, the cells exhibit a marker pattern similar to MSC, but do not differentiate into either osteocytes or adipocytes, under conditions where MSC would differentiate into osteocytes or adipocytes, respectively. The MSC used for comparison in these assays are, in one embodiment, MSC that have been harvested from BM and cultured under 2D conditions. In other embodiments, the MSC used for comparison have been harvested from BM and cultured under 2D conditions, followed by 3D conditions. In more particular embodiments, the mesenchymal-like ASC are maternal cells, or in other embodiments are fetal cells, or in other embodiments are a mixture of fetal cells and maternal cells.

Optional Additional Preparation Steps

In certain embodiments, further steps of purification or enrichment for ASC may be performed as part of the cell preparation process. Such methods include, but are not limited to, cell sorting using markers for ASC and/or, in various embodiments, mesenchymal stromal cells or mesenchymal-like ASC.

Cell sorting, in this context, refers to any a procedure, whether manual, automated, etc., that selects cells on the basis of their expression of one or more markers, their lack of expression of one or more markers, or a combination thereof. Those skilled in the art will appreciate that data from one or more markers can be used individually or in combination in the sorting process.

Buffers

Those skilled in the art will appreciate that a variety of isotonic buffers may be used for washing cells and similar uses. Hank's Balanced Salt Solution (HBSS; Life Technologies) is only one of many buffers that may be used.

Non-limiting examples of base media useful in 2D and 3D culturing include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. In certain embodiments, DMEM is used. These and other useful media are available from GIBCO, Grand Island, N.Y., USA and Biological Industries, Bet HaEmek, Israel, among others.

In some embodiments, whether or not inflammatory cytokines are added, the medium may be supplemented with additional substances. Non-limiting examples of such substances are serum, which is, in some embodiments, fetal serum of cows or other species, which is, in some embodiments, 5-15% of the medium volume. In certain embodiments, the medium contains 1-5%, 2-5%, 3-5%, 1-10%, 2-10%, 3-10%, 4-15%, 5-14%, 6-14%, 6-13%, 7-13%, 8-12%, 8-13%, 9-12%, 9-11%, or 9.5%-10.5% serum, which may be fetal bovine serum, or in other embodiments another animal serum. In still other embodiments, the medium is serum-free.

Alternatively or in addition, the medium may be supplemented by growth factors, vitamins (e.g. ascorbic acid), cytokines, salts (e.g. B-glycerophosphate), steroids (e.g. dexamethasone) and hormones e.g., growth hormone, erythropoietin, thrombopoietin, interleukin 3, interleukin 7, macrophage colony stimulating factor, c-kit ligand/stem cell factor, osteoprotegerin ligand, insulin, insulin-like growth factor, epidermal growth factor, fibroblast growth factor, nerve growth factor, ciliary neurotrophic factor, platelet-derived growth factor, and bone morphogenetic protein.

It will be appreciated that additional components may be added to the culture medium. Such components may be antibiotics, antimycotics, albumin, amino acids, and other components known to the art for the culture of cells.

Those skilled in the art will appreciate that animal sera and other sources of growth factors are often included in growth media. In some cases, animal sera may contain inflammatory cytokines, which, in general, are not present in large amounts. Some preparations utilize a serum that is treated, for example, with charcoal, so as to remove most or all of the cytokines present. In any event, reference herein to "added cytokines", "medium containing cytokines", or the like, does not encompass the presence of cytokines present in animal sera that is customarily included in the medium.

It will also be appreciated that in certain embodiments, when the described ASC are intended for administration to a human subject, the cells and the culture medium (e.g., with the above described medium additives) are substantially xeno-free, i.e., devoid of any animal contaminants e.g., mycoplasma. For example, the culture medium can be supplemented with a serum-replacement, human serum and/or synthetic or recombinantly produced factors.

Where added cytokines are utilized, the various media described herein, i.e. (as applicable) the 2D growth medium, the first 3D growth medium, and/or the second 3D growth medium, may be, in certain embodiments, independently selected from each of the described embodiments relating to medium composition. In certain embodiments, the only difference between the first and second 3D growth media is the presence of the added cytokines. In other embodiments, the first and second 3D growth media differ in other respects. In various embodiments, any medium suitable for growth of cells in a bioreactor may be used.

Tissue Sources and Cell Characteristics

In certain embodiments, the described ASC are mesenchymal stromal cells (MSC). These cells may, in some embodiments, be isolated from many adult tissues, such as placenta, bone marrow and adipose. In further embodiments, the cells are human MSC as defined by The Mesenchymal and Tissue Stem Cell Committee of the International Society for Cellular Therapy (Dominici et al, 2006), based on the following 3 criteria: 1. Plastic-adherence when maintained in standard culture conditions (a minimal essential medium plus 20% fetal bovine serum (FBS)). 2. Expression of the surface molecules CD105, CD73 and CD90, and lack of expression of CD45, CD34, CD14 or CD11b, CD79a or CD19 and HLA-DR. 3. Differentiation into osteoblasts, adipocytes and chondroblasts in vitro.

Alternatively or in addition, the described ASC are mesenchymal-like ASC, which exhibit a marker pattern similar to "classical" MSC, but do not differentiate into osteocytes, under conditions where "classical" MSC would differentiate into osteocytes. In other embodiments, the cells exhibit a marker pattern similar to MSC, but do not differentiate into adipocytes, under conditions where MSC would differentiate into adipocytes. In still other embodiments, the cells exhibit a marker pattern similar to MSC, but do not differentiate into either osteocytes or adipocytes, under conditions where MSC would differentiate into osteocytes or adipocytes, respectively. The MSC used for comparison in these assays are, in one embodiment, MSC that have been harvested from bone marrow (BM) and cultured under 2D conditions. In other embodiments, the MSC used for comparison have been harvested from bone marrow (BM) and cultured under 2D conditions, followed by 3D conditions. In more particular embodiments, the mesenchymal-like ASC are maternal cells, or in other embodiments are fetal cells.

In various embodiments, ASC may be derived, for example, from placenta; adipose tissue; bone marrow; peripheral blood; umbilical cord blood; synovial fluid; synovial membranes; spleen; thymus; mucosa (for example nasal mucosa); limbal stroma; ligaments, for example the periodontal ligament; scalp; hair follicles, testicles; embryonic yolk sac; and amniotic fluid, all of which are known to include ASC. In certain embodiments, the source of the ASC is a non-fetal source, for example maternal cells from the placenta or somatic tissue from a pediatric or adult donor, for example adipose tissue, bone marrow, peripheral blood, umbilical cord blood, synovial fluid, synovial membranes, and ligaments such as the periodontal ligament. In some embodiments, the ASC are human ASC, while in other embodiments, they may be animal ASC. In particular embodiments, the ASC are derived from placental tissue or are derived from adipose tissue.

Placenta-Derived Stromal Cells

Except where indicated otherwise herein, the terms "placenta", "placental tissue", and the like refer to any portion of the placenta. Placenta-derived adherent cells may be obtained, in various embodiments, from either fetal or, in other embodiments, maternal regions of the placenta, or in other embodiments, from both regions. More specific embodiments of maternal sources are the decidua basalis and the decidua parietalis. More specific embodiments of fetal sources are the amnion, the chorion, and the villi. In certain embodiments, tissue specimens are washed in a physiological buffer [e.g., phosphate-buffered saline (PBS) or Hank's buffer]. Single-cell suspensions can be made, in other embodiments, by treating the tissue with a digestive enzyme (see below) or/and physical disruption, a non-limiting example of which is mincing and flushing the tissue parts through a nylon filter or by gentle pipetting (Falcon, Becton, Dickinson, San Jose, Calif.) with washing medium. In some embodiments, the tissue treatment includes use of a DNAse, a non-limiting example of which is Benzonase® nuclease from Merck. In other embodiments, placental cells may be obtained from a full-term or pre-term placenta.

In some embodiments, residual blood is removed from the placenta before cell harvest. This may be done by a variety of methods known to those skilled in the art, for example by perfusion. The term "perfuse" or "perfusion" as used herein refers to the act of pouring or passaging a fluid over or through an organ or tissue. In certain embodiments, the placental tissue may be from any mammal, while in other embodiments, the placental tissue is human.

A convenient source of placental tissue is a post-partum placenta (e.g., less than 10 hours after birth), however, a variety of sources of placental tissue or cells may be contemplated by the skilled person. In other embodiments, the placenta is used within 8 hours, within 6 hours, within 5 hours, within 4 hours, within 3 hours, within 2 hours, or within 1 hour of birth. In certain embodiments, the placenta is kept chilled prior to harvest of the cells. In other embodiments, prepartum placental tissue is used. Such tissue may be obtained, for example, from a chorionic villus sampling or by other methods known in the art. Once placental cells are obtained, they are, in certain embodiments, allowed to adhere to an adherent material (e.g., configured as a surface) to thereby isolate adherent cells. In some embodiments, the donor is 35 years old or younger, while in other embodiments, the donor may be any woman of childbearing age.

Placental Cell Preparations Enriched for Fetal Cells or Maternal Cells

In other embodiments, the described ASC are a placental preparation containing both maternal and fetal cells. In certain embodiments, the preparation is enriched for maternal cells. The present inventor has found that under many standard culture conditions, maternal cells tend to dominate 2D and 3D cultures after several passages. In other embodiments, at least 60%, at least 65%, at least 70%, at least 75%, at least 80%, at least 85%, at least 90%, at least 92%, at least 95%, at least 96%, at least 97%, at least 98%, at least 99%, at least 99.5%, at least 99.7%, or at least 99.9% of the described cells are maternally-derived cells. Lack of expression of CD200, as measured by flow cytometry, using an isotype control to define negative expression, can be used as a marker of fetal cells. In other embodiments, the cells are substantially entirely fetal cells, or are substantially entirely maternal cells. "Substantially entirely", in this context, refers to a lack of detectable presence of other cell types (maternal or fetal, respectively) by standard fluorescence-activated cell sorting assays.

Methods of preparing and characterizing maternal-derived and fetal-derived ASC are described in WO 2011/064669, which is incorporated herein by reference. In some embodiments, maternal and fetal placental ASC are identified based on genotype and/or karyotype (e.g., FISH) analysis. For example, ASC from a placenta of a male embryo can be separated into fetal and maternal cells based on karyotype analysis (i.e., XX cells are maternal while XY cells are fetal). In some embodiments, ASC derived from a fetal portion of the placenta (e.g., consisting of or comprising chorionic villi) express CD200. In other embodiments, not more than 3.5%, not more than 3%, not more than 2%, or not more than 1% of the adherent stromal cells from a maternal placental cell preparation express CD200 as measured by flow cytometry using an isotype control to define negative expression.

In other embodiments, the preparation is enriched for fetal cells. In more specific embodiments, the mixture contains at least 70% fetal cells. In more specific embodiments, at least about 30%, 35%, 40%, 45%, 50%, 55%, 60%, 65%, 75%, 80%, 85%, 90%, 95%, 96%, 97%, 98%, 99% or 100% of the cells are fetal cells. Expression of CD200, as measured by flow cytometry, using an isotype control to define negative expression, can be used as a marker of fetal cells under some conditions. In yet other embodiments, at least 60%, at least 65%, at least 70%, at least 75%, at least 80%, at least 85%, at least 90%, at least 92%, at least 95%, at least 96%, at least 97%, at least 98%, at least 99%, at least 99.5%, at least 99.7%, or at least 99.9% of the described cells are fetal cells.

Adipose-Derived Stromal Cells

As used herein the phrase "adipose tissue" refers to a connective tissue which comprises fat cells (adipocytes). Adipose tissue-derived adherent stromal cells may be extracted, in various embodiments, by a variety of methods known to those skilled in the art, for example those described in U.S. Pat. No. 6,153,432, which is incorporated herein by reference. The adipose tissue may be derived, in other embodiments, from omental/visceral, mammary, gonadal, or other adipose tissue sites. In some embodiments, the adipose can be isolated by liposuction.

In other embodiments, ASC may be derived from adipose tissue by treating the tissue with a digestive enzyme (non-limiting examples of which are collagenase, trypsin, dispase, hyaluronidase or DNAse); and ethylenediaminetetraacetic acid (EDTA). The cells may be, in some embodiments, subjected to physical disruption, for example using a nylon or cheesecloth mesh filter. In other embodiments, the cells are subjected to differential centrifugation directly in media or over a Ficoll™, Percoll™, or other particulate gradient (see U.S. Pat. No. 7,078,230, which is incorporated herein by reference).

Stromal Cells from Other Sources

As mentioned, in some embodiments the source of the ASC is a non-fetal source, for example maternal cells from the placenta or somatic tissue from a pediatric or adult donor, for example adipose tissue, bone marrow, peripheral blood, umbilical cord blood, synovial fluid, synovial membranes, and ligaments such as the periodontal ligament. Those skilled in the art will appreciate in light of the present disclosed that ASC may be extracted from various body tissues, using standard techniques such as physical and/or enzymatic tissue disruption, in some embodiments followed by marker-based cell sorting, and then may be subjected to the culturing methods described herein.

Identifying Characteristics

As mentioned, in some embodiments, the described ASC do not differentiate into osteocytes, under conditions where "classical" mesenchymal stem cells would differentiate into osteocytes. In some embodiments, the conditions are incubation with a solution containing 0.1 micromolar (mcM) dexamethasone, 0.2 mM ascorbic acid, and 10 mM glycerol-2-phosphate, in plates coated with vitronectin and collagen, for 17 days. In still other embodiments, the conditions are incubation with a solution containing 10 mcM dexamethasone, 0.2 mM ascorbic acid, 10 mM glycerol-2-phosphate, and 10 nM Vitamin D, in plates coated with vitronectin and collagen, for 26 days. The aforementioned solutions will typically contain cell culture medium such as DMEM+10% serum or the like, as will be appreciated by those skilled in the art.

In other embodiments, the described cells do not differentiate into adipocytes, under conditions where mesenchymal stem cells would differentiate into adipocytes. In some embodiments, as provided herein, the conditions are incubation of adipogenesis induction medium, namely a solution containing 1 mcM dexamethasone, 0.5 mM 3-Isobutyl-1-methylxanthine (IBMX), 10 mcg/ml insulin, and 100 mcM indomethacin, added on days 1, 3, 5, 9, 11, 13, 17, 19, and 21, while the medium is replaced with adipogenesis maintenance medium, namely a solution containing 10 mcg/ml insulin, on days 7 and 15, for a total of 25 days. In still other embodiments, as provided herein, a modified adipogenesis induction medium, containing 1 mcM dexamethasone, 0.5 mM IBMX, 10 mcg/ml insulin, and 200 mcM indomethacin is used, and the incubation is for a total of 26 days. The aforementioned solutions will typically contain cell culture medium such as DMEM+10% serum or the like, as will be appreciated by those skilled in the art.

In certain embodiments, in vitro, the described ASC stimulate endothelial cell proliferation, or in another embodiment inhibit T cell proliferation, or in another embodiment perform both activities. In other embodiments, in vivo, the cells stimulate angiogenesis, or in another embodiment exhibit immunosuppressive activity (in some embodiments, particularly for T cell responses), and or in another embodiment support hematopoietic stem cell (HSC) engraftment, or in other embodiments any 2 of the above in vivo characteristics, or in other embodiments all 3 of the above in vivo characteristics. Each combination is considered to be a separate embodiment. In certain embodiments, as provided herein, when 750 human umbilical cord endothelial cells (HUVEC) are incubated for 4 days under normoxic conditions at 37° C. on a layer of the ASC, proliferation of the HUVEC cells is at least 120%, at least 125%, at least 130%, at least 140%, at least 150%, and least 160%, or at least 180% of the level observed in the absence of ASC.

According to some embodiments, the described ASC are capable of suppressing an immune reaction in the subject. Methods of determining the immunosuppressive capability of a cell population are well known to those skilled in the art. For example, a mixed lymphocyte reaction (MLR) may be performed, for example as exemplified herein. In an exemplary, non-limiting MLR assay, cord blood (CB) mononuclear cells, for example human cells or cells from another species, are incubated with irradiated cord blood cells (iCB), peripheral blood-derived monocytes (PBMC; for example human PBMC or PBMC from another species), in the presence or absence of a cell population to be tested. CB cell replication, which correlates with the intensity of the immune response, can be measured by a variety of methods known in the art, for example by $^3$H-thymidine uptake. Reduction of the CB cell replication when co-incubated with test cells indicates an immunosuppressive capability. Alternatively, a similar assay can be performed with peripheral blood (PB)-derived MNC, in place of CB cells. Alternatively or in addition, secretion of pro-inflammatory and anti-inflammatory cytokines by blood cell populations (such as CB cells or PBMC) can be measured when stimulated (for example by incubation with non-matched cells, or with a non-specific stimulant such as PHA), in the presence or absence of the ASC. In certain embodiments, for example in the case of human ASC, as provided herein, when 150,000 of the ASC are co-incubated for 48 hours with 50,000 allogeneic PBMC, followed by a 5-hour stimulation with 1.5 mcg of LPS, the amount of IL-10 secretion by the PBMC is at least 120%, at least 130%, at least 150%, at least 170%, at least 200%, or at least 300% of the amount observed with LPS stimulation in the absence of ASC.

In other embodiments, the described cells exhibit a spindle shape when cultured under 2D conditions.

Alternatively or additionally, the cells may express a marker or a collection of markers (e.g. surface marker) characteristic of MSC or mesenchymal-like stromal cells. Examples of surface markers include but are not limited to CD105 (UniProtKB Accession No. P17813), CD29 (UniProtKB Accession No. P05556), CD44 (UniProtKB Accession No. P16070), CD73 (UniProtKB Accession No. P21589), and CD90 (UniProtKB Accession No. P04216). Examples of markers expected to be absent from stromal cells are CD3 (UniProtKB Accession Nos. P09693 [gamma chain] P04234 [delta chain], P07766 [epsilon chain], and P20963 [zeta chain]), CD4 (UniProtKB Accession No. P01730), CD34 (UniProtKB Accession No. P28906), CD45 (UniProtKB Accession No. P08575), CD80 (UniProtKB Accession No. P33681), CD19 (UniProtKB Accession No. P15391), CD5 (UniProtKB Accession No. P06127), CD20 (UniProtKB Accession No. P11836), CD11B (UniProtKB Accession No. P11215), CD14 (UniProtKB Accession No. P08571), CD79-alpha (UniProtKB Accession No. B5QTD1), and HLA-DR (UniProtKB Accession Nos. P04233 [gamma chain], P01903 [alpha chain], and P01911 [beta chain]). All UniProtKB entries were accessed on Jul. 7, 2014, except where indicated otherwise. Those skilled in the art will appreciate that the presence of complex antigens such as CD3 and HLA-DR may be detected by antibodies recognizing any of their component parts, such as, but not limited to, those described herein.

In certain embodiments, over 90% of the described cells are positive for CD29, CD90, and CD54. In other embodiments, over 85% of the described cells are positive for CD73 and CD105; and over 65% of the described cells are positive for CD49. In yet other embodiments, less than 1% of the described cells are positive for CD14, CD19, CD31, CD34, CD39, CD45, HLA-DR, and GlyA; at least 30% of the cells are positive for CD200; less than 6% of the cells are positive for GlyA; and less than 20% of the cells are positive for SSEA4. In more specific embodiments, over 90% of the described cells are positive for CD29, CD90, and CD54; over 85% of the cells are positive for CD73 and CD105; and over 65% of the cells are positive for CD49. In still other embodiments, over 90% of the described cells are positive for CD29, CD90, and CD54; over 85% of the cells are positive for CD73 and CD105; over 65% of the cells are positive for CD49; less than 1% of the cells are positive for CD14, CD19, CD31, CD34, CD39, CD45, HLA-DR, GlyA; at least 30% of the cells are positive for CD200; less than 6% of the cells are positive for GlyA; and less than 20% of the cells are positive for SSEA4.

In other embodiments, each of CD73, CD29, and CD105 is expressed by more than 90% of the cells. In still other embodiments, each of CD44, CD73, CD29, and CD105 is expressed by more than 90% of the cells. In yet other embodiments, each of CD34, CD45, CD19, CD14 and HLA-DR is expressed by less than 3% of the cells. In other embodiments, each of CD73, CD29, and CD105 is expressed by more than 90% of the cells, and each of CD34, CD45, CD19, CD14 and HLA-DR is expressed by less than 3% of the cells. In other embodiments, each of CD44, CD73, CD29, and CD105 is expressed by more than 90% of the cells, and each of CD34, CD45, CD19, CD14 and HLA-DR is expressed by less than 3% of the cells.

In other embodiments, each of CD73, CD29, and CD105 is expressed by more than 90% of the cells; and the cells do not differentiate into osteocytes, after incubation for 17 days with a solution containing 0.1 mcM dexamethasone, 0.2 mM ascorbic acid, and 10 mM glycerol-2-phosphate, in plates coated with vitronectin and collagen. In yet other embodiments, each of CD34, CD45, CD19, CD14 and HLA-DR is expressed by less than 3% of the cells; and the cells do not differentiate into osteocytes, after incubation under the aforementioned conditions. In other embodiments, each of CD73, CD29, and CD105 is expressed by more than 90% of the cells, and of CD34, CD45, CD19, CD14 and HLA-DR is expressed by less than 3% of the cells; and the cells do not differentiate into osteocytes, after incubation under the aforementioned conditions. In still other embodiments, the conditions are incubation for 26 days with a solution containing 10 mcM dexamethasone, 0.2 mM ascorbic acid, 10 mM glycerol-2-phosphate, and 10 nM Vitamin D, in plates coated with vitronectin and collagen. The aforementioned solutions will typically contain cell culture medium such as DMEM+10% serum or the like, as will be appreciated by those skilled in the art.

In other embodiments, each of CD73, CD29, and CD105 is expressed by more than 90% of the cells; and the cells do not differentiate into adipocytes, after incubation in adipogenesis induction medium, namely a solution containing 1 mcM dexamethasone, 0.5 mM 3-Isobutyl-1-methylxanthine (IBMX), 10 mcg/ml insulin, and 100 mcM indomethacin, on days 1, 3, 5, 9, 11, 13, 17, 19, and 21; and replacement of the medium with adipogenesis maintenance medium, namely a solution containing 10 mcg/ml insulin, on days 7 and 15, for a total of 25 days. In yet other embodiments, each of CD34, CD45, CD19, CD14 and HLA-DR is expressed by less than 3% of the cells; and the cells do not differentiate into adipocytes, after incubation under the aforementioned conditions. In other embodiments, each of CD73, CD29, and CD105 is expressed by more than 90% of the cells, each of CD34, CD45, CD19, CD14 and HLA-DR is expressed by less than 3% of the cells; and the cells do not differentiate into adipocytes, after incubation under the aforementioned conditions. In still other embodiments, a modified adipogenesis induction medium, containing 1 mcM dexamethasone, 0.5 mM IBMX, 10 mcg/ml insulin, and 200 mcM indomethacin is used, and the incubation is for a total of 26 days. The aforementioned solutions will typically contain cell culture medium such as DMEM+10% serum or the like, as will be appreciated by those skilled in the art.

Alternatively or in addition, the cells express the marker D7-fib, which is typically expressed on fibroblasts. Antibodies against D7-fib are commercially available from Acris Antibodies, Herford, Germany.

In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99% of the ASC express a marker selected from CD73, CD90, CD29, and CD105, or in other embodiments 2 or more of these markers, or in other embodiments 3 or more of these markers, or in other embodiments all four of these markers in combination.

According to some embodiments, the ASC express CD200, or, in other embodiments, lack expression thereof. In still other embodiments, less than 30%, 25%, 20%, 15%, 10%, 8%, 6%, 5%, 4%, 3%, or 2%, 1%, or 0.5% of the adherent cells express CD200. In yet other embodiments, greater than 30%, 35%, 40%, 45%, 50%, 55%, 60%, 65%, 70%, 75%, 80%, 85%, 90%, 92%, 94%, 95%, 96%, 97%, 98%, 99%, or 99.5% of the adherent cells express CD200.

According to some embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99% of the adherent stromal cells do not express a marker selected from CD3, CD4, CD45, CD80, HLA-DR, CD11b, CD14, CD19, CD34, and CD79-alpha, or in other embodiments do not express 2 or more of these markers, or in other embodiments 3 or more of these markers, or in other embodiments 4 or more of these markers, or in other embodiments 5 or more of these markers, or in other embodiments 6 or more of these markers, or in other embodiments 7 or more of these markers, or in other embodiments 8 or more of these markers, or in other embodiments 9 or more of these markers, or in other embodiments all ten of these markers.

In various embodiments, the ASC that are used in the described therapeutic methods express or secrete (as appropriate for each protein) c-kit ligand/stem cell factor (SCF; Uniprot Accession no. P21583, Receptor-type tyrosine-protein kinase FLT3 (Flt-3; Uniprot Accession no. P36888), and/or Aldehyde dehydrogenase X (ALDH X; Uniprot Accession no. P30837), each of which represents a separate embodiment. In some embodiments, the cells have been incubated in a 3D culture, and they express at least 2, 3, 4, 5, 6, 7, 8, 9, 10, 11, or even 12 fold higher of at least one of these proteins than that expressed or secreted by ASC of the same cell type (e.g. placenta, adipose tissue, or bone marrow) incubated in a 2D culture only. In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99% of the cells express or secrete at least one, in other embodiments at least 2, in other embodiments at least 3, in other embodiments all four of the aforementioned proteins.

Additionally or alternatively, the ASC that are used secrete or express IL-6, eukaryotic translation elongation factor 2 (EEEF2), reticulocalbin 3, EF-hand calcium binding domain (RCN2), and/or calponin 1 basic smooth muscle (CNN1). In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, in other embodiments greater than 99%, of the cells express or secrete at least one, in other embodiments at least 2, in other embodiments at least 3, in other embodiments at least 4, in other embodiments all five of the aforementioned proteins.

Additionally or alternatively, the ASC that are used express low or undetectable amounts of heterogeneous nuclear ribonucleoprotein H1 (Hnrph1), CD44 antigen isoform 2 precursor, 3 phosphoadenosine 5 phosphosulfate synthase 2 isoform a (Papss2), and/or ribosomal protein L7a (rpL7a). In more specific embodiments, greater than 50%, in other embodiments greater than 55%, in other embodiments greater than 60%, in other embodiments greater than 65%, in other embodiments greater than 70%, in other embodiments greater than 75%, in other embodiments greater than 80%, in other embodiments greater than 85%, in other embodiments greater than 90%, in other embodiments greater than 95%, in other embodiments greater than 96%, in other embodiments greater than 97%, in other embodiments greater than 98%, of the cells do not express or secrete at least one, in other embodiments at least 2, in other embodiments at least 3, in other embodiments all four of the aforementioned proteins.

In certain embodiments, the ASC have been transfected with one or more therapeutic factors. In other embodiments, the cells have not been transfected with any exogenous genetic material.

In yet other embodiments, the population of ASC that is used in the described therapeutic methods secretes elevated levels of Vascular Endothelial Growth Factor (VEGF). In some embodiments, the VEGF secretion is measured after removing the cells from the bioreactor. In certain embodiments, the VEGF secretion is at least 1.5-fold, at least 2-fold, at least 2.5-fold, at least 3-fold, at least 4-fold, or at least 5-fold as high as cells prepared in the absence of added cytokines. In certain embodiments, as provided herein, VEGF secretion is measured by incubating $1\times10^6$ ASC for 24 hours under standard conditions, then replacing the medium with EBM-2 medium and incubating for 24 hours under hypoxic conditions (1% $O_2$). In more specific embodiments, at least 180 picograms (pg), at least 190 pg, at least 200 pg, at least 250 pg, at least 300 pg, at least 400 pg, at least 500 pg, at least 600 pg, at least 800 pg, at least 1000 pg, at least 1200 pg, at least 1500 pg, at least 2000 pg, at least 3000 pg, at least 4000 pg, at least 5000 pg, at least 6000 pg, or at least 7000 pg of VEGF are secreted by the cells under these conditions. In still other embodiments is provided use of a bioreactor, comprising the VEGF-secreting ASC, in the preparation of a medicament for the described therapeutic indications. In some embodiments, the bioreactor further comprises a synthetic 3D substrate. In other embodiments is provided a pharmaceutical composition, comprising the VEGF-secreting ASC, for treatment, prevention, or inhibition of muscle wasting syndrome or muscle loss. In certain embodiments, the composition further comprises a pharmacologically acceptable excipient. In further embodiments, the excipient is a cryoprotectant, or is a carrier protein. Alternatively or in addition, the composition is frozen.

In yet other embodiments, the population of ASC that is used in the described therapeutic methods secretes elevated levels of Interleukin-6 (IL-6; UniProt No. P05231). In some embodiments, the IL-6 secretion is measured after removing the cells from the bioreactor. In certain embodiments, the IL-6 secretion is at least 2-fold, at least 3-fold, at least 4-fold, at least 5-fold, at least 6-fold, or at least 8-fold, or at least 10-fold as high as cells prepared in the absence of added cytokines. In certain embodiments, as provided herein, IL-6 secretion is measured by incubating $1\times10^6$ ASC for 24 hours under standard conditions, then replacing the medium with EBM-2 medium and incubating for 24 hours under hypoxic conditions (1% 02). In more specific embodiments, at least 20 picograms (pg), at least 30 pg, at least 50 pg, at least 70 pg, at least 100 pg, at least 150 pg, at least 200 pg, at least 300 pg, at least 400 pg, at least 500 pg, at least 700 pg, at least 1000 pg, or at least 2000 pg of IL-6 are secreted by the cells under these conditions. In still other embodiments is provided use of a bioreactor, comprising the IL-6-secreting ASC, in the preparation of a medicament for the described therapeutic indications. In some embodiments, the bioreactor further comprises a synthetic 3D substrate. In other embodiments is provided a pharmaceutical composition, comprising the IL-6-secreting ASC, for treatment, prevention, or inhibition of muscle wasting or muscle loss. In certain embodiments, the composition further comprises a pharmacologically acceptable excipient. In further embodiments, the excipient is a cryoprotectant, or is a carrier protein. Alternatively or in addition, the composition is frozen.

In yet other embodiments, the population of ASC that is used in the described therapeutic methods secretes elevated levels of MCP-1 (Monocyte chemoattractant protein 1; UniProt No. P13500). In some embodiments, as provided herein, MCP-1 secretion is measured during the last day of incubation in the bioreactor. In certain embodiments, the MCP-1 secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In still other embodiments is provided use of a bioreactor, comprising the MCP-1-secreting ASC, in the preparation of a medicament for the described therapeutic indications. In some embodiments, the bioreactor further comprises a synthetic 3D substrate. In other embodiments is provided a pharmaceutical composition, comprising the MCP-1-secreting ASC, for treatment, prevention, or inhibition of muscle wasting or muscle loss. In certain embodiments, the composition further comprises a pharmacologically acceptable excipient. In further embodiments, the excipient is a cryoprotectant, or is a carrier protein. Alternatively or in addition, the composition is frozen.

In yet other embodiments, the population of ASC that is used in the described therapeutic methods secretes elevated levels of GM-CSF. In some embodiments, as provided herein, GM-CSF secretion is measured during the last day of incubation in the bioreactor. In certain embodiments, the GM-CSF secretion is at least 2-fold, at least 3-fold, at least 4-fold, at least 5-fold, at least 6-fold, or at least 8-fold, at least 10-fold, at least 15-fold, at least 20-fold, or at least 30-fold as high as cells prepared in the absence of added cytokines. In still other embodiments is provided is provided use of a bioreactor, comprising the GM-CSF-secreting ASC, in the preparation of a medicament for the described therapeutic indications. In some embodiments, the bioreactor further comprises a synthetic 3D substrate. In other embodiments is provided a pharmaceutical composition, comprising the GM-CSF-secreting ASC, for treatment, prevention, or inhibition of muscle wasting or muscle loss. In certain embodiments, the composition further comprises a pharmacologically acceptable excipient. In further embodiments, the excipient is a cryoprotectant, or is a carrier protein. Alternatively or in addition, the composition is frozen.

In yet other embodiments, the population of ASC that is used ASC in the described therapeutic methods secretes elevated levels of RANTES (C-C motif chemokine 5; UniProt No. P13501). In some embodiments, the RANTES secretion is measured after removing the cells from the bioreactor. In certain embodiments, the RANTES secretion is at least 2-fold, at least 3-fold, at least 4-fold, at least 5-fold, at least 6-fold, or at least 8-fold, at least 10-fold, at least 15-fold, at least 20-fold, at least 30-fold, at least 50-fold, at least 70-fold, at least 100-fold, at least 150-fold, at least 200-fold, at least 300-fold, at least 500-fold, at least 700-fold, or at least 1000-fold as high as cells prepared in the absence of added cytokines. In certain embodiments, as provided herein, RANTES secretion is measured by incubating $5 \times 10^5$ ASC for 24 hours under standard conditions, then replacing the medium with serum medium and incubating for an additional 24 hours. In more specific embodiments, at least 20 picograms (pg), at least 30 pg, at least 50 pg, at least 70 pg, at least 100 pg, at least 150 pg, at least 200 pg, at least 300 pg, at least 400 pg, at least 500 pg, at least 700 pg, at least 1000 pg, at least 1500 pg, at least 2000 pg, at least 3000 pg, at least 4000 pg, at least 5000 pg, at least 6000 pg, at least 8000 pg, at least 10,000 pg, at least 15,000 pg, or at least 20,000 pg, of RANTES are secreted by the cells under these conditions. In still other embodiments is provided use of a bioreactor, comprising the RANTES-secreting ASC, in the preparation of a medicament for the described therapeutic indications. In some embodiments, the bioreactor further comprises a synthetic 3D substrate. In other embodiments is provided a composition, comprising the RANTES-secreting ASC, for treatment, prevention, or inhibition of muscle wasting or muscle loss. In certain embodiments, the composition further comprises a pharmacologically acceptable excipient. In further embodiments, the excipient is a cryoprotectant, or is a carrier protein. Alternatively or in addition, the composition is frozen.

In still other embodiments, the utilized ASC may be allogeneic, or in other embodiments, the cells may be autologous. In other embodiments, the cells may be fresh or, in other embodiments, frozen (e.g., cryo-preserved).

Also provided is use of conditioned media (CM) produced by the described methods, and, in other embodiments, pharmaceutical compositions comprising the described CM, for the described therapeutic indications. Those skilled in the art will appreciate that, in certain embodiments, various bioreactors may be used to prepare CM, including but not limited to plug-flow bioreactors, and stationary-bed bioreactors (Kompier R et al. Use of a stationary bed reactor and serum-free medium for the production of recombinant proteins in insect cells. Enzyme Microb Technol. 1991. 13(10): 822-7). Pharmaceutical compositions comprising CM may be freely combined with any of the described embodiments for culture method steps, cell characteristics, or therapeutic parameters.

It is clarified that each embodiment of the described CM may be freely combined with each embodiment relating to a therapeutic method or pharmaceutical composition.

Exosomes and Uses Thereof

Also provided herein is use of exosomes secreted by the described ASC, for the described therapeutic indications. Methods of isolating exosomes are well known in the art, and include, for example, immuno-magnetic isolation, for example as described in Clayton A et al, 2001; Mathias R A et al, 2009; and Crescitelli R et al, 2013.

In some embodiments, the exosomes are harvested from a 3D bioreactor in which the ASC have been incubated. In some embodiments, the culture in the 3D bioreactor includes inflammatory cytokines. In other embodiments, the 3D culture utilizes standard medium. Alternatively or in addition, the ASC are placenta-derived ASC, which may be, in more specific embodiments, enriched in fetal cells or in maternal cells.

Alternatively, the cells are cryopreserved following 3D culture, or in other embodiments following 2D culture, and then are thawed, after which the exosomes are isolated. In some embodiments, after thawing, the exosomes are cultured in 2D culture, from which the exosomes are harvested. In certain embodiments, the 2D culture is performed in the presence of inflammatory cytokines, which may be, in various embodiments, any of the cytokines mentioned herein. In other embodiments, the 2D culture utilizes standard medium. Alternatively or in addition, the ASC are placenta-derived ASC, which may be, in more specific embodiments, enriched in fetal cells or, in other embodiments, in maternal cells.

In other embodiments is provided a method of treatment, prevention, or inhibition of a muscle wasting disorder, muscle wasting syndrome, or muscle loss, comprising the step of administering to the subject a pharmaceutical composition comprising the described exosomes. Also provided is a composition for treatment, prevention, or inhibition of muscle wasting syndrome or muscle loss, comprising the described exosomes. Provided in addition is use of the described exosomes in the preparation of a medicament for treatment, prevention, or inhibition of muscle wasting syndrome or muscle loss.

It is clarified that each embodiment of the described exosomes may be freely combined with each embodiment relating to a therapeutic method or pharmaceutical composition.

Pharmaceutical Compositions

The cells, CM, or exosomes can be administered as a part of a pharmaceutical composition that further comprises one or more pharmaceutically acceptable carriers. Hereinafter, the term "pharmaceutically acceptable carrier" refers to a carrier or a diluent that does not cause significant irritation to a subject and does not abrogate the biological activity and properties of the administered cells. Examples, without limitations, of carriers are propylene glycol, saline, emulsions and mixtures of organic solvents with water. In some embodiments, the pharmaceutical carrier is an aqueous solution of saline. In other embodiments, the composition further comprises a pharmacologically acceptable excipient.

In further embodiments, the excipient is an osmoprotectant or cryoprotectant, an agent that that protects cells from the damaging effect of freezing and ice formation, which may in some embodiments be a permeating compound, non-limiting examples of which are dimethyl sulfoxide (DMSO), glycerol, ethylene glycol, formamide, propanediol, poly-ethylene glycol, acetamide, propylene glycol, and adonitol; or may in other embodiments be a non-permeating compound, non-limiting examples of which are lactose, raffinose, sucrose, trehalose, and d-mannitol. In other embodiments, both a permeating cryoprotectant and a non-permeating cryoprotectant are present. In other embodiments, the excipient is a carrier protein, a non-limiting example of which is albumin. In still other embodiments, both an osmoprotectant and a carrier protein are present; in certain embodiments, the osmoprotectant and carrier protein may be the same compound. Alternatively or in addition, the composition is frozen. The cells may be any embodiment of ASC mentioned herein, each of which is considered a separate embodiment.

Since non-autologous cells may in some cases induce an immune reaction when administered to the body, several approaches have been developed to reduce the likelihood of rejection of non-autologous cells. These include either suppressing the recipient immune system or encapsulating the non-autologous cells in immune-isolating, semipermeable membranes before transplantation. This may be done, in various embodiments, whether or not the ASC themselves engraft in the host. For example, the majority of the cells may, in various embodiments, not survive after engraftment for more than 3 days, more than 4 days, more than 5 days, more than 6 days, more than 7 days, more than 8 days, more than 9 days, more than 10 days, or more than 14 days.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF-alpha blockers, biological agents that antagonize one or more inflammatory cytokines, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, and tramadol.

One may, in various embodiments, administer the pharmaceutical composition in a systemic manner (as detailed herein). Alternatively, one may administer the pharmaceutical composition locally, for example, via injection of the pharmaceutical composition directly into a tissue region of a patient, such as, in non-limiting embodiments, an atrophied muscle. In other embodiments, the cells are administered intramuscularly, intravenously (IV), subcutaneously (SC), or intraperitoneally (IP), each of which is considered a separate embodiment. In still other embodiments, the pharmaceutical composition is administered intralymphatically, for example as described in U.S. Pat. No. 8,679,834 in the name of Eleuterio Lombardo and Dirk Buscher, which is hereby incorporated by reference.

In other embodiments, for injection, the described cells may be formulated in aqueous solutions, preferably in physiologically compatible buffers such as Hank's solution, Ringer's solution, or physiological salt buffer, optionally in combination with medium containing cryopreservation agents.

Depending on the severity and responsiveness of the muscle wasting to be treated, dosing can be a single or, in other embodiments, 2, 3, 4, at least 2, at least 3, at least 4, more than 4, or a plurality of administrations, with a course of treatment lasting from several days to several weeks or, in other embodiments, until alleviation of the disease state is achieved. In some embodiments, the interval between doses is between 1 hour and 10 days; in other words, the doses are spaced by a period not less than 1 hour and not more than 10 days. In other embodiments, the interval between doses is between 2 hours and 10 days; between 3 hours and 10 days; between 4 hours and 10 days; between 6 hours and 10 days; between 8 hours and 10 days; between 12 hours and 10 days; between 24 hours and 10 days; between 1-24 hours; between 2-24 hours; between 3-24 hours; between 4-24 hours; between 6-24 hours; between 8-24 hours; between 12-24 hours; between 1-5 days; between 1-10 days; between 1-15 days; between 1-20 days; between 2-5 days; between 2-10 days; between 2-15 days; between 2-20 days; between 2-30 days; between 3-10 days; between 3-15 days; between 3-20 days; between 3-30 days; or between 5-30 days.

In certain embodiments, following administration, the majority of the cells, in other embodiments more than 60%, more than 70%, more than 80%, more than 90%, more than 95%, more than 96%, more than 97%, more than 98%, or more than 99% of the cells are no longer detectable within the subject 1 month after administration.

In certain embodiments, compositions including the described preparations formulated in a compatible pharmaceutical carrier are prepared, placed in an appropriate container, and labeled for treatment of an indicated condition, for example muscle wasting syndrome.

The described compositions may, if desired, be packaged in a container that is accompanied by instructions for administration. The container may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The described ASC are, in some embodiments, suitably formulated as pharmaceutical compositions which can be suitably packaged as an article of manufacture. Such an article of manufacture comprises a packaging material which comprises a label for use in anti-muscle wasting syndrome therapy, as described herein.

A typical dosage of the described ASC used alone ranges, in some embodiments, from about 10 million to about 500 million cells per administration, for a human subject. For example, the dosage can be, in some embodiments, 10, 20, 30, 40, 50, 60, 70, 80, 90, 100, 125, 150, 175, 200, 225, 250, 275, 300, 325, 350, 375, 400, 425, 450, 475, or 500 million cells or any amount in between these numbers. It is further understood that a range of adherent stromal cells can be used including from about 10 to about 500 million cells, from about 100 to about 400 million cells, from about 150 to about 300 million cells. Accordingly, disclosed herein are therapeutic methods, the method comprising administering to a subject a therapeutically or prophylactically effective amount of ASC, wherein the dosage administered to the subject is 10, 20, 30, 40, 50, 60, 70, 80, 90, 100, 125, 150, 175, 200, 225, 250, 275, 300, 325, 350, 375, 400, 425, 450, 475, or 500 million cells or, in other embodiments, between 150 million to 300 million cells. ASC, compositions comprising ASC, and/or medicaments manufactured using ASC can be administered, in various embodiments, in a series of 1, 2, 3, 4, 5, 6, 7, 8, 9, 10, 11, 12, 13, 14, 15, 1-10, 1-15, 1-20, 2-10, 2-15, 2-20, 3-20, 4-20, 5-20, 5-25, 5-30, 5-40, or 5-50 injections, or more.

In still other embodiments is provided use of a bioreactor, comprising the described ASC, in preparing a medicament described herein. In some embodiments, the bioreactor further comprises a synthetic material that is a 3D substrate. The cells may be any embodiment of ASC mentioned herein, each of which is considered a separate embodiment.

It is clarified that each embodiment of the described ASC may be freely combined with each embodiment relating to a therapeutic method or pharmaceutical composition.

In still other embodiments, the described conditioned medium is used in any of the described therapeutic methods. Each embodiment of conditioned medium may be freely combined with each embodiment relating to a therapeutic method or pharmaceutical composition.

In certain embodiments, the subject may be administered with additional therapeutic agents or cells as part of the described methods and compositions. In certain embodiments, the additional therapeutic agent is agent that treats muscle wasting syndrome or muscle loss, non-limiting examples of which are testosterone, nonsteroidal selective androgen receptor modulators (SARMs) (Mohler et al, 2009), megestrol acetate (MA), meloxicam, eicosapentaenoic acid (EPA), Ghrelin, thalidomide, pentoxifylline, melatonin, clenbuterol, estrogens, growth hormones, vitamin D, angiotensin-converting enzyme inhibitors, soluble activin receptor type IIB (ActRIIB), myostatin inhibitors, and medroxyprogesterone. Non-limiting examples of SARMs are found in United States Patent Application Publ. Nos. 2013/0034562, 2014/0051764, 2014/0011774, 2009/0264534, and 2007/0123563, and 2006/0035965, the contents of which are incorporated by reference herein.

Also disclosed herein are kits and articles of manufacture that are drawn to reagents that can be used in practicing the methods disclosed herein. The kits and articles of manufacture can include any reagent or combination of reagent discussed herein or that would be understood to be required or beneficial in the practice of the disclosed methods, including ASC. In another aspect, the kits and articles of manufacture may comprise a label, instructions, and packaging material, for example for treatment, prevention, or inhibition of muscle wasting syndrome or muscle loss.

Subjects

In certain embodiments, the subject treated by the described methods and compositions is a human. In other embodiments, the subject may be an animal.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Reference is now made to the following examples, which together with the above descriptions illustrate certain embodiments in a non-limiting fashion.

Example 1

Production and Culturing of Adherent Stromal Cells

Overview:
The manufacturing process for the final cell product consisted of 2 stages:
Stage 1, the intermediate cell stock (ICS) production, contains the following steps:
1. Extraction of ASCs from the placenta.
2. 2-dimensional cell growth for up to 12 population doublings.
3. Cell concentration, formulation, filling and cryopreservation.

Stage 2, the thawing of the ICS and further culture, contains the following steps:
1. 2-dimensional cell growth of the thawed ICS for up to 8 additional doublings.
2. 3-dimensional cell growth in bioreactor/s and harvest from bioreactor/s up to 10 additional doublings.
3. Downstream processing: cell concentration, washing, formulation, filling and cryopreservation.

The procedure included periodic testing of the growth medium for sterility and contamination.
Production of ICS
Step 1-1—Extraction of Adherent Stromal Cells (ASC)
Placentas were obtained from donors up to 35 years old, who were pre-screened for hepatitis B, hepatitis C, HIV-1 and HIV-2, HTLV-1 and HTLV-2, and syphilis. The donor placenta was maintained sterile and cooled until the initiation of the extraction process.

Within 4 hours of the delivery, the placenta was placed with the maternal side facing upwards and was cut into pieces (sized ~1 cm$^3$), which were washed thoroughly with isotonic buffer) containing gentamicin.

The washed pieces were incubated for 1-3 hours with collagenase and DNAse in isotonic buffer.
Culture medium (DMEM], 10% filtered FBS and L-Glutamine) supplemented with gentamicin, was added, and the digested tissue was coarsely filtered through a sterile stainless steel sieve and centrifuged.
The cells were suspended in culture medium, seeded in flasks, and incubated at 37° C. in a tissue culture incubator under humidified conditions supplemented with 5% $CO_2$.

After 2-3 days, cells were washed twice with Phosphate-Buffered Saline (PBS), and the culture medium was replaced.

Cells were incubated for an additional 4-5 days prior to the first passage.

Step 1-2—Initial 2-Dimensional Culturing

Passage 1:

Cells were detached using trypsin, centrifuged, and seeded at a culture density of $3\pm0.2\times10^3$ cells/cm$^2$ in tissue culture flasks, in culture medium lacking gentamicin.

Subsequent Passages:

When the culture reached 60-90% confluence, cells were passaged as described above.

Step 1-3—Cell Concentration, Washing, Formulation, Filling and Cryopreservation

Following the final passage, the resulting cell suspension was centrifuged and re-suspended in culture medium at a final concentration of $20-40\times10^6$ cells/milliliter (mL). The cell suspension was diluted 1:1 with 2D Freezing Solution (20% DMSO, 80% FBS), and the cells were cryopreserved in 10% DMSO, 40% FBS, and 50% full DMEM. The temperature was reduced in a controlled rate freezer (1° C./min down to −80° C. followed by 5° C./min down to −120° C.), and the cells were stored in a liquid nitrogen freezer to produce the ICS.

Production of Cell Product

Step 2-1: Additional Two-Dimensional (2D) Cell Culturing.

The ICS was thawed, diluted with culture medium, and cultured for up to 10 additional doublings, passaging when reaching 60-90% confluence, then were harvested for seeding in the bioreactor.

Step 2-2: Three Dimensional (3D) Cell Growth in Bioreactor/s

From the cell suspension, 1 or 2 bioreactors were seeded. Each bioreactor contained FibraCel® carriers (New Brunswick Scientific) made of polyester and polypropylene, and culture medium. $170\times10^6$ cells were seeded into each 2.8-liter bioreactor.

The growth medium in the bioreactor/s was kept at the following conditions: temp: $37\pm1°$ C., Dissolved Oxygen (DO): $70\pm10\%$ and pH $7.4\pm0.2$. Filtered gases (Air, $CO_2$, $N_2$ and $O_2$) were supplied as determined by the control system in order to maintain the target DO and pH values.

After seeding, the medium was agitated with stepwise increases in the speed, up to 150-200 RPM by 24 hours. Perfusion was initiated several hours after seeding and was adjusted on a daily basis in order to keep the glucose concentration constant at approximately 550 mg\liter.

Cell harvest was performed at the end of the growth phase (approximately day 6). Bioreactors were washed for 1 minute with pre-warmed sterile PBS, and cells were detached. The cells were found to be over 90% maternally-derived cells.

Step 2-3: Downstream Processing: Cell Concentration, Washing, Formulation, Filling and Cryopreservation In some experiments, the cell suspension underwent concentration and washing, using suspension solution (5% w/v human serum albumin [HSA] in isotonic solution) as the wash buffer, and diluted 1:1 with 2× 3D-Freezing solution (20% DMSO v/v and 10% HSA w/v in isotonic solution) to a concentration of $10-20\times10^6$ cells/ml. The temperature of the vials was gradually reduced, and the vials were stored in a gas-phase liquid nitrogen freezer.

Example 2

Osteocyte and Adipose Differentiation Assays

Methods

Bone Marrow Adherent Cells—

Bone marrow (BM) adherent cells were obtained from aspirated sterna marrow of hematologically healthy donors undergoing open-heart surgery or BM biopsy. Marrow aspirates were diluted 3-fold in HBSS) and subjected to Ficoll-Hypaque (Robbins Scientific Corp. Sunnyvale, Calif.) density gradient centrifugation. Thereafter, marrow mononuclear cells (<1.077 μm/cm$^3$) were collected, washed 3 times in HBSS, and resuspended in growth media [DMEM (Biological Industries, Beit HaEmek, Israel) supplemented with 10% FCS (GIBCO BRL), $10^{-4}$ M mercaptoethanol (Merck, White House Station, N.J.), Pen-Strep-Nystatin mixture (100 U/ml:100 μg/m1:1.25 un/ml; Beit HaEmek), 2 mM L-glutamine (Beit HaEmek)]. Cells from individual donors were incubated separately in tissue culture flasks (Corning, Acton, Mass.) at 37° C. (5% $CO_2$) with weekly change of culture media. Cells were passaged every 3-4 days using 0.25% trypsin-EDTA (Beit HaEmek). Following 2-40 passages, when reaching 60-80% confluence, cells were collected for analysis.

TABLE 1

Osteogenesis medium components

| Component | Stock conc. | Amount | Final conc. |
|---|---|---|---|
| DMEM low glucose (Invitrogen, Gibco) | | 8.7 ml | 87% |
| Serum (heat inactivated) | | 1 ml | 10% |
| dexamethasone | 1 mM | 1 μl | 0.1 μM |
| Ascorbic Acid-2-Phosphate solution | 0.1M | 20 μL | 0.2 mM |
| Glycerol-2-Phosphate Solution | 1M | 100 μL | 10 mM |
| L-glutamine | X 100 | 100 μl | X 1 |
| Pen & Strep | X 100 | 100 μl | X 1 |

Induction of Osteogenesis

Placenta-derived cells or BM-derived cells were plated (200,000 cells per well) in 1 ml growth medium comprising DMEM (Invitrogen, Gibco), 10% FCS (Invitrogen, Gibco), 2 Mm L-glutamine (Sigma-Aldrich), 45 μg/ml Gentamicin-IKA (Teva Medical) and 0.25 μg/ml Fungizone® (Invitrogen, Gibco) in wells coated with a coating mixture containing 12 μg/ml vitronectin and 12 μg/ml collagen, which was provided with the Millipore Mesenchymal Stem Cell Osteogenesis Kit. Cells were grown until 100% confluent (typically overnight) before adding osteogenic differentiation medium.

On differentiation day 1, growth medium was aspirated and replaced with 1 ml osteogenesis induction medium, which was replaced with fresh medium every 2-3 days for 14-17 days. Osteocytes were fixed and stained with Alizarin Red Solution.

In other experiments, a modified osteogenesis induction medium was used, having the components listed in Table 2, including Vitamin D, for 26 days.

TABLE 2

Modified osteogenesis medium components

| Component | Stock conc. | Amount | Final conc. |
|---|---|---|---|
| DMEM high glucose (Biological Industries, Bet Haemek, Israel) | | 8.7 ml | 87% |

TABLE 2-continued

Modified osteogenesis medium components

| Component | Stock conc. | Amount | Final conc. |
|---|---|---|---|
| L-glutamine | X 100 | 100 µl | X 1 |
| Serum (heat inactivated) |  | 1 ml | 10% |
| Dexamethasone (Chemicon) | 10 mM | 10 µl | 10 µM |
| Ascorbic Acid-2-Phosphate solution (Chemicon) | 0.1M | 20 µl | 0.2 mM |
| Glycerol-2-Phosphate Solution (Chemicon) | 1M | 100 µL | 10 mM |
| Vitamin D (Sigma) | 10 µM | 10 µL | 10 nM |
| Gentamycin (Biological Industries, Bet Haemek, Israel) | X 100 | 100 µl | X 1 |

Induction of Adipogenesis

Adipogenesis was carried out according to the instructions provided with the Chemicon Adipogenesis Kit (cat no. scr020, Millipore, Mass., USA)

Adipogenesis Induction Medium

Adipogenesis induction and maintenance medium were freshly prepared prior to every medium exchange, using the components depicted in Tables 3 and 4, below.

TABLE 3

Adipogenesis induction medium components

| Component | Stock conc. | Amount | Final conc. |
|---|---|---|---|
| DMEM low glucose (Biological Industries, Bet Haemek, Israel) |  | 4.4 ml | 90% |
| Serum (heat inactivated) |  | 0.5 ml | 10% |
| Dexamethasone (Sigma) | 10 mM | 0.5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 50 µl | 100 µM |
| Pen & Strep | X 100 | 50 µl | X 1 |

TABLE 4

Adipogenesis maintenance medium components

| Component | Stock conc. | Amount | Final conc. |
|---|---|---|---|
| DMEM low glucose |  | 4.4 ml | 90% |
| Serum (heat inactivated) |  | 0.5 ml | 10% |
| Insulin | 10 mg/ml | 5 µL | 10 µg/ml |
| Pen & Strep | X 100 | 50 µl | X 1 |

Cell Growth

Placenta-derived or BM-derived cells were plated (200,000 cells per well) in 1 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) and were grown until 100% confluent (typically overnight) before initiating adipogenesis differentiation.

On differentiation day 1, growth medium was aspirated and replaced with 1 ml adipogenesis induction medium, which was replaced with fresh induction or maintenance medium every 2-3 days for a total of 25 days, according to the schedule in Table 5.

TABLE 5

Adipogenesis differentiation schedule

| Day | Medium |
|---|---|
| 1 | Adipogenesis Induction medium |
| 3 | Adipogenesis Induction medium |
| 5 | Adipogenesis Induction medium |
| 7 | Adipogenesis Maintenance medium |
| 9 | Adipogenesis Induction medium |
| 11 | Adipogenesis Induction medium |
| 13 | Adipogenesis Induction medium |
| 15 | Adipogenesis Maintenance medium |
| 17 | Adipogenesis Induction medium |
| 19 | Adipogenesis Induction medium |
| 21 | Adipogenesis Induction medium |

On day 25, adipocytes were fixed and stained with oil red solution.

Modified Adipogenesis Induction Medium

The modified adipogenesis induction medium contained the components depicted in Table 6, and was used for a total of 26 days.

TABLE 6

Modified adipogenesis induction medium components

| Component | Stock con | Amount | Final conc. |
|---|---|---|---|
| DMEM low glucose |  | 4.4 ml | 90% |
| Serum (heat inactivated) |  | 0.5 ml | 10% |
| Dexamethasone (Sigma) | 1 mM | 5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 200 µl | 200 µM |
| Gentamycine (Biological Industries) |  | 10 µl |  |

Results

Osteocyte Induction.

Incubation of BM-derived adherent cells in osteogenic induction medium resulted in differentiation of over 50% of the BM cells, as demonstrated by positive alizarin red staining. On the contrary, none of the placental-derived cells exhibited signs of osteogenic differentiation.

Next, a modified osteogenic medium comprising Vitamin D and higher concentrations of dexamethasone was used. Over 50% of the BM cells underwent differentiation into osteocytes, while none of the placental-derived cells exhibited signs of osteogenic differentiation.

Adipocyte Induction.

Adipocyte differentiation of placenta- or BM-derived adherent cells in adipocyte induction medium resulted in differentiation of over 50% of the BM-derived cells, as demonstrated by positive oil red staining and by typical morphological changes (e.g. accumulation of oil droplets in the cytoplasm). In contrast, none of the placental-derived cells differentiated into adipocytes.

Next, a modified medium containing a higher indomethacin concentration was used. Over 50% of the BM-derived cells underwent differentiation into adipocytes. In contrast, none of the placental-derived cells exhibited morphological changes typical of adipocytes.

Example 3

Marker Expression on Adherent Stromal Cells

Methods (Examples 3-5)

FACS analysis of membrane markers was performed by staining cells with monoclonal antibodies (MAbs). 400,000-

600,000 cells were suspended in 1 ml flow cytometer buffer in a 5 ml test tube and incubated for 15 minutes at room temperature (RT), in the dark, with each of the following MAbs: PE-conjugated anti-human CD29 MAb (Becton Dickinson), PE-conjugated anti human CD73 MAb (Becton Dickinson), PE-conjugated anti human CD105 MAb (Becton Dickinson), PE-conjugated anti human CD90 MAb (Becton Dickinson), PE-conjugated anti-human CD45 MAb (Becton Dickinson), PE-conjugated anti-human CD19 MAb (Becton Dickinson), PE-conjugated anti human CD14 MAb (Becton Dickinson), PE-conjugated anti human HLA-DR MAb (Becton Dickinson), PE-conjugated anti human CD34 MAb (Becton Dickinson), PE-conjugated anti human CD31 MAb (Becton Dickinson), PE-conjugated anti-human CD200 MAb (Becton Dickinson), Isotype IgG2beta PE-conjugated (Becton Dickinson), Isotype IgG1alpha PE-conjugated (Becton Dickinson); and anti-CD106, anti-CD54, anti-CD56, anti-CD49d, anti-glyA, and anti-CD39, all PE-conjugated and from Becton Dickinson; Alexa Fluor®-conjugated anti-SSEA4 (eBioscience), and IgG3 kappa isotype control (Biolegend).

Cells were washed twice with flow cytometer buffer, resuspended in 400 microliters (mcl) flow cytometer buffer, and analyzed by flow cytometry.

Human/Human Mixed Lymphocyte Reaction (MLR)

$2 \times 10^5$ peripheral blood (PB) derived MNC (from donor A) were stimulated with equal amount of irradiated (3000 Rad) PB derived MNCs (from donor B). Increasing amounts of stromal cells were added to the cultures. Three replicates of each group were seeded in 96-well plates. Cells were cultured in RPMI 1640 medium containing 20% FBS. Plates were pulsed with 1 microCurie (mcC) $^3$H-thymidine during the last 18 hrs. of the 5-day culturing. Cells were harvested over a fiberglass filter and thymidine uptake was quantified with scintillation counter.

Human/Rat PBMC Proliferation Assay

ASC were seeded in a 96-well plate and incubated for 24 hours. Peripheral blood mononuclear cells (PBMCs) were labeled with carboxyfluorescein succinimidyl ester (CFSE), a fluorescent cell staining dye, which diffuses into cells and tags proliferating cells, activated with PHA, and co-cultured with ASC for 5 days. Maximum proliferation (100%) was arbitrarily set as the proliferation of PBMC cells after PHA stimulation in the absence of ASC. Flow cytometry methods were used to determine the percentage of PBMCs. Results may be presented both as % Inhibition of T Cell Proliferation (% ITCP) or as Relative Percent of % ITCP, with the latter calculated by dividing the % ITCP of the tested sample by that of the reference batch.

For CFSE staining, PB-MNC cells were stained for CFSE (Molecular Probes) for proliferation measurement before culturing. Cells were collected after 5 days, and the intensity of CFSE staining was detected by Flow Cytometry.

ELISA

MNCs (isolated from peripheral blood) were stimulated with 5 microgram (mcg)/ml ConA (Sigma), 0.5 mcg/ml LPS (SIGMA), or 10 mcg/ml PHA (SIGMA) in the presence of stromal cells under a humidified 5% $CO_2$ atmosphere at 37° C. Supernatants were collected and subjected to cytokine analysis using ELISA kits for IFN-gamma (DIACLONE), TNF-alpha (DIACLONE), and IL-10 (DIACLONE).

Results

Expression of Cellular Markers on Isolated Cells— the surface antigens expressed by the isolated cells were examined using monoclonal antibodies. The cells expressed CD73, CD29, and CD105, and did not express the markers CD34, CD45, CD19, CD14, and HLA-DR. More specifically, all the positive markers were expressed by more than 90% of the cells, and all the negative markers were expressed by less than 3% of the cells.

Furthermore, the cells did not express endothelial markers as shown by negative staining for the two endothelial markers CD31 and KDR. However, expression of a fibroblast-typical marker, D7-fib, was evident.

Example 4

Immunogenicity and Immunomodulatory Properties of ASC

Figure 2:
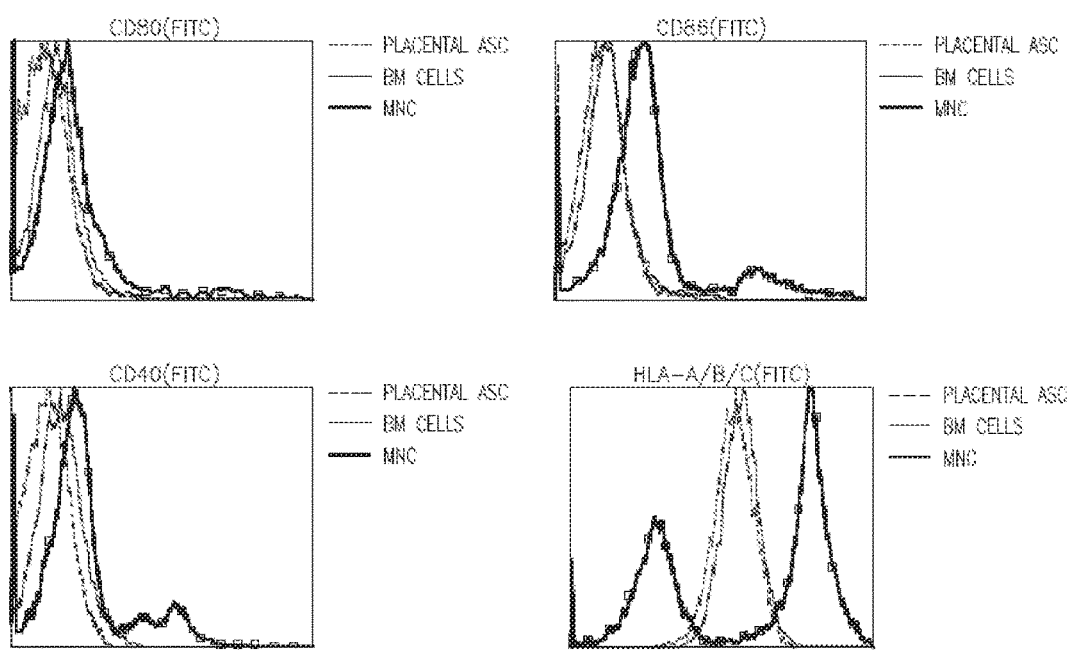
FIG. 2 contains plots of expression of stimulatory and co-stimulatory molecules on ASC. Upper left: Expression of CD80. Upper right: Expression of CD86. Lower left. Expression of CD40. Lower right: Expression of HLA-A/B/C. Negative controls were prepared with relevant isotype fluorescence molecules. Dotted, light, and heavy lines indicate marker-expression by placental ASC, bone marrow (BM) cells, and mononuclear cells (MNC), respectively

The expression of co-stimulatory molecules on ASC was measured. FACS analysis demonstrated the absence of CD80, CD86 and CD40 on the cell membranes (FIGS. 2A-C). Moreover, the cells expressed low levels HLA class I molecules, as detected by staining for HLA A/B/C (FIG. 2D).

Figure 3:
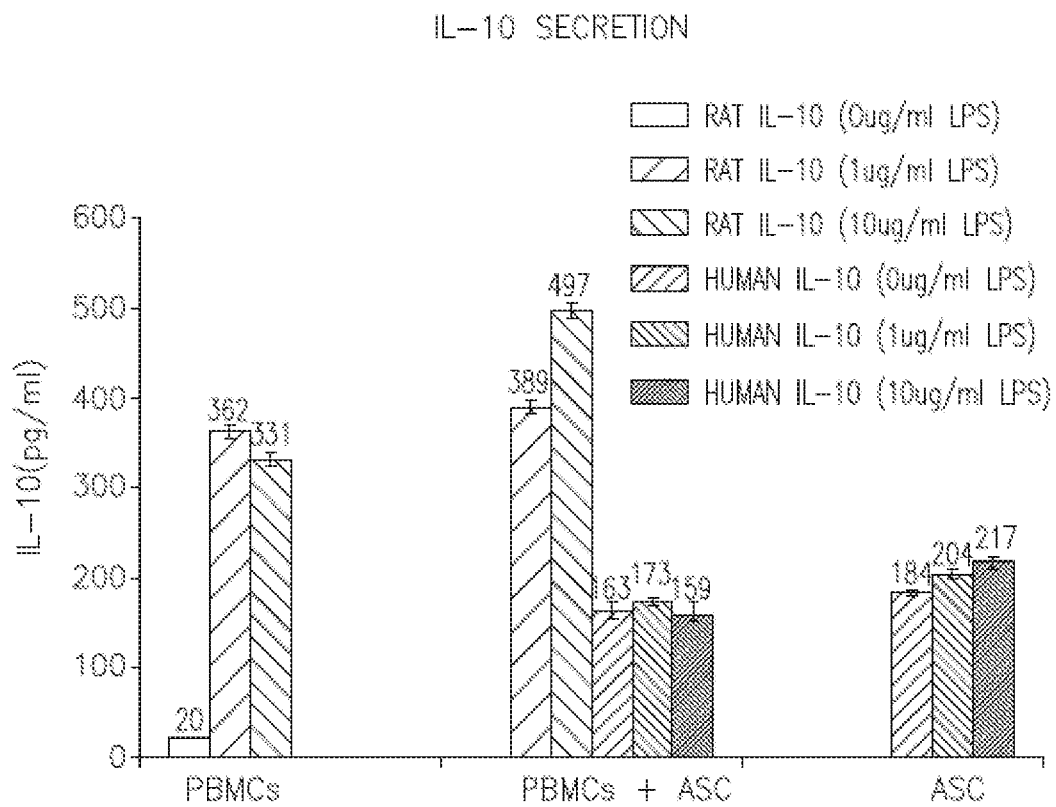
FIG. 3 is a graph of secretion of IL-10 by PBMC in the absence or presence of ASC. Bars in each group, from left to right are: 1-3: Rat IL-10 after stimulation with 0, 1, or 10 mcg/ml LPS; and 4-6: human IL-10 after stimulation with 0, 1, or 10 mcg/ml LPS.

To further investigate the immunogenicity and the immunomodulatory properties of the cells, human/rat Mixed Lymphocyte Reaction (MLR) tests were performed. Rat PBMC were stimulated with LPS (lipopolysaccharide) in the absence or presence of (human) ASC, and secretion of IL-10 by the PBMC was measured. ASC increased the IL-10 secretion (FIG. 3).

Figure 4A:
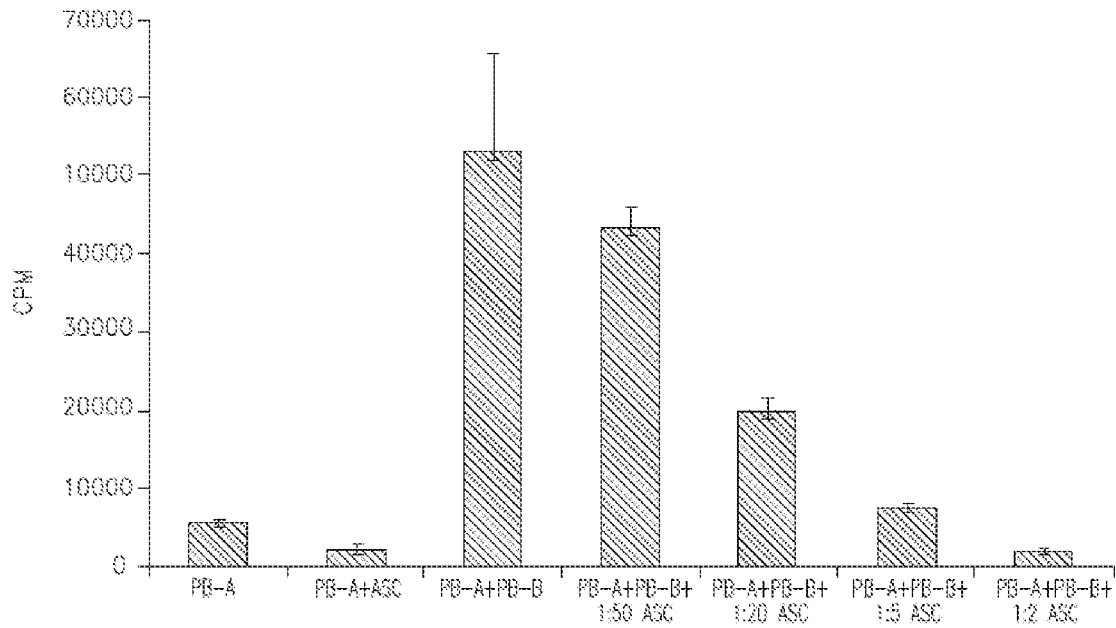
FIGS. 4A-B are charts depicting lymphocyte proliferation, measured by [$^3$H]thymidine incorporation. A. $2\times10^5$ peripheral blood (PB)-derived MNC (donor A) were stimulated with an equal number of irradiated (3000 Rad) PB-derived MNCs (donor B) in a MLR test, in the presence of different amounts of ASC. B. PB-derived MNCs stimulated with ConA (1.5 mg/ml). For (A) and (B), three replicates of each sample were performed.
Figure 4B:
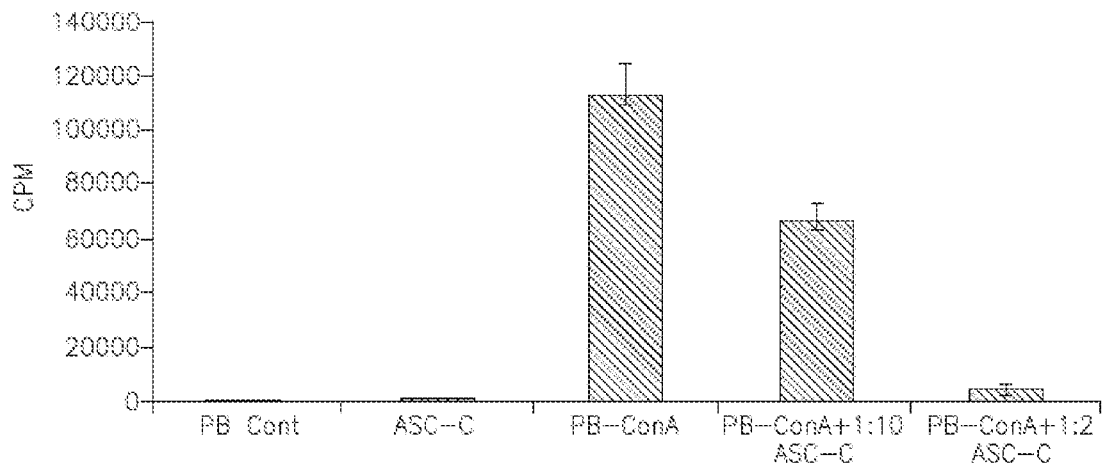

MLR performed with 2 different donors also showed that the ASC escaped allorecognition and reduced lymphocyte proliferation, as measured by thymidine incorporation, following mitogenic stimuli, such as allogeneic cells (FIG. 4A) and Concanavalin A (Con A) (FIG. 4B) and Phytohemagglutinin (PHA; typically at least 25% inhibition relative to PHA alone), and non-specific stimulation by anti-CD3 and anti-CD28. The reduction in lymphocyte proliferation was dose dependent with the number of ASC.

Next, PBMC were stimulated by PHA using the Transwell® method (which prevents cell-to-cell contact but enables the diffusion of cytokines between the two compartments). The inhibition of proliferation was maintained even in this assay, showing that cell-to-cell contact was not necessary for the inhibition.

Example 5

Adherent Stromal Cells Alter Cytokine Secretion by PBMC

Figure 5A:
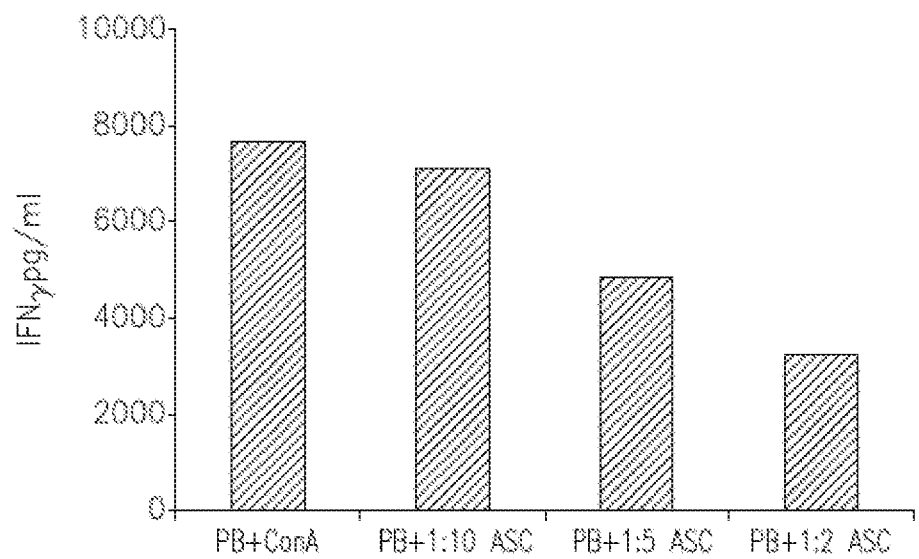
FIGS. 5A-C are charts depicting ASC regulation of pro- and anti-inflammatory cytokine secretion by human MNCs (isolated from peripheral blood). A-B depict secretion of IFN-gamma (A) and TNF-alpha (B) stimulation with ConA. C depicts secretion of IFN-gamma, TNF-alpha and IL-10 (left, middle, and right bars in each series, respectively) following stimulation with LPS. Supernatants were analyzed by ELISA
Figure 5B:
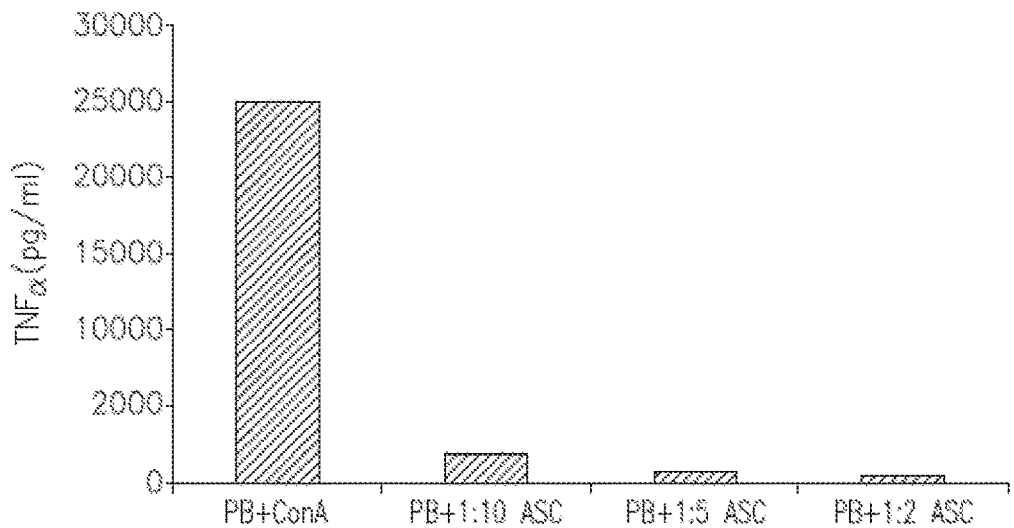
Figure 5C:
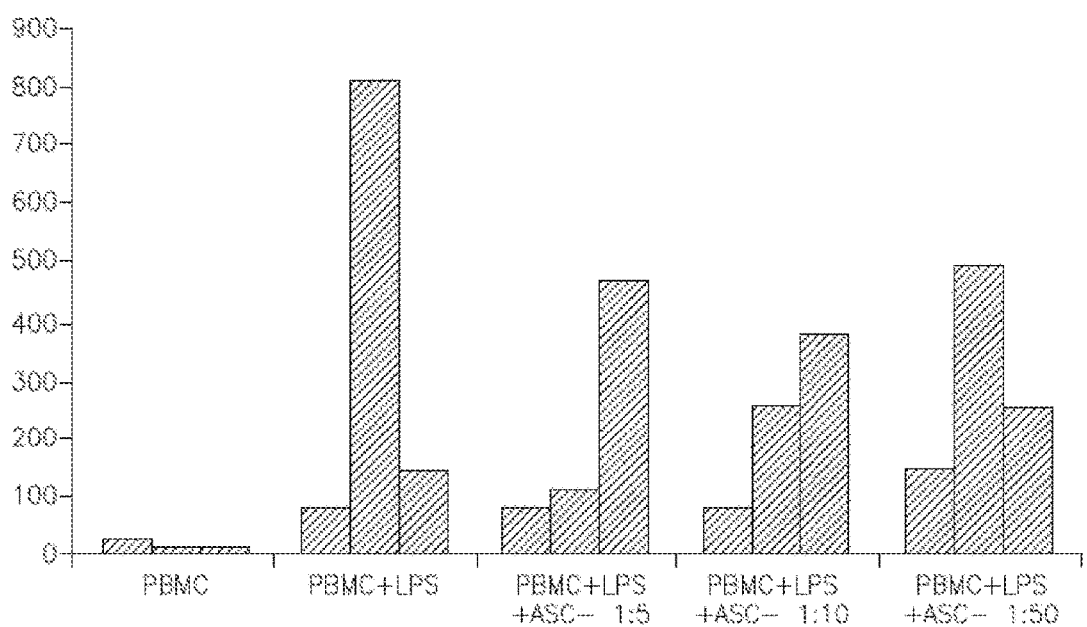

Additional co-culture studies were performed to test the effect of ASC on secretion of cytokines by lymphocytes. Culturing of PB-derived mononuclear cells (PBMC) with ASC slightly reduced IFN-gamma secretion and dramatically reduced TNF-alpha secretion by the PBMC, even when only low amounts of ASC were present (FIGS. 5A-B). Under conditions of LPS stimulation, the ASC increased secretion of IL-10 by PBMC, while decreasing their secretion of TNF-alpha, in a dose-dependent manner (FIG. 5C).

Example 6

ASC Stimulate Endothelial Cell Proliferation

Protocol—Endothelial Cell Proliferation (ECP) Assay:

ASC were prepared as described in Example 1, harvested by vibration, as described in PCT International Application Publ. No. WO 2012/140519, and were cryopreserved. $1 \times 10^6$ thawed ASC were seeded in 2 ml DMEM medium. After 24 hours (hr), the medium was replaced with EBM-2 medium (Lonza Group Ltd, Basel, Switzerland), and cells were incubated under hypoxic conditions (1% $O_2$) for an additional 24 hr, after which the conditioned media was collected. In parallel, 750 human umbilical cord endothelial cells (HUVEC) were seeded, incubated for 24 hr, and then incubated with the conditioned media, for 4 days under normoxic conditions at 37° C. After removal of the conditioned medium, the proliferation of the HUVEC cells was assayed using the AlamarBlue® fluorescent assay. Results are presented as the percent ECP (% ECP) observed after PHA stimulation in the absence of ASC (arbitrarily set at 100%).

Results

Figure 6:
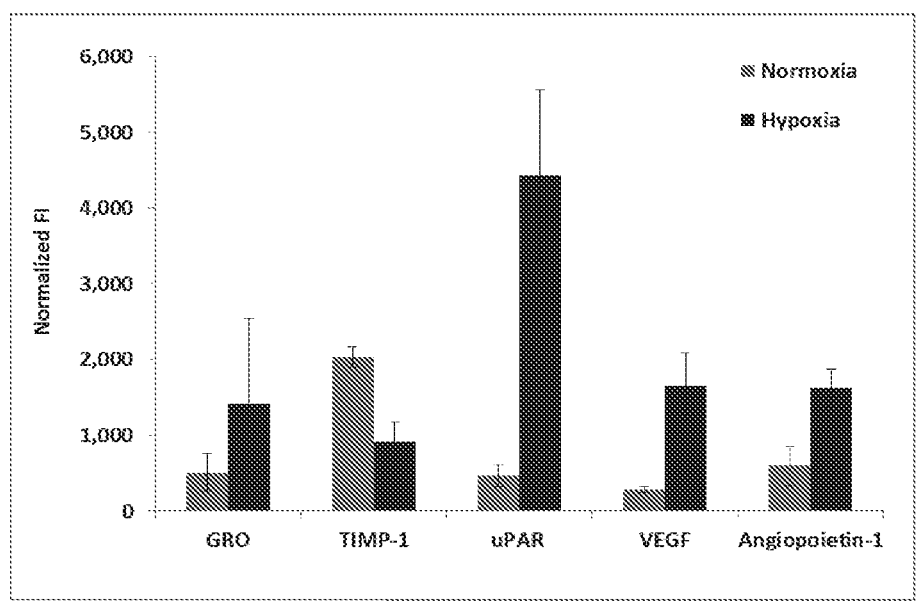
FIG. 6 is a graph of secretion profile of ASC under normoxic or hypoxic conditions.

ASC cultured under normoxic or hypoxic conditions were tested for protein secretion, using Cytokine (Human) Antibody Array C Series 4000 (RayBio). Secretion of several pro-angiogenic factors was up-regulated under hypoxic conditions, as shown in FIG. 6.

In additional experiments, various batches of ASC were co-incubated with HUVEC cells to test their effect on ECP. Stimulation of ECP was observed, typically at least 135% of the ECP observed in the absence of ASC.

Example 7

Treatment of ASC with Pro-Inflammatory Cytokines During 3D Culturing

Methods

General Experimental Protocol.

ASC were obtained from the placenta and cultured under 2D conditions, then under 3D conditions, and were then harvested, all as described in Example 1, with the following deviation: 36 hours before the end of the 3D culture (typically on day 5 or 6), the medium was replaced with DMEM, with or without the addition of 10 nanograms/milliliter (ng/ml) Tumor Necrosis Factor alpha (TNF-alpha), 10 ng/ml Interferon-Gamma (IFN-g), and/or 10% FBS (see Table 7), and the bioreactor was incubated in batch mode (or, in selected experiments, in perfusion mode) for an additional day. Levels of secreted cytokines were measured in the bioreactor medium, using the RayBio® Human Cytokine Array kit.

TABLE 7

Incubation conditions that were tested.

| Designation | Cytokines | FBS |
|---|---|---|
| 1 | None | NO |
| 2 | None | YES |
| 3 | TNF | NO |
| 4 | TNF | YES |
| 5 | TNF + IFN | NO |
| 6 | TNF + IFN | YES |

In other experiments, levels of secreted cytokines were measured in the conditioned medium (CM) from a hypoxic incubation, as described in the context of the ECP assay in the previous Example.

Quantitative detection of secreted proteins: IL-6 was quantitatively measured using the human IL-6 immunoassay Quantikine® ELISA kit (R&D Systems). VEGF was quantitatively measured using the Human VEGF immunoassay Quantikine® kit (R&D Systems).

Results

In a series of experiments testing various conditions side-by-side, adherent stromal cells (ASC) were incubated in a bioreactor as described in the previous Examples. On the last day of the bioreactor incubation, the medium was replaced by medium containing or lacking added TNF-alpha and/or IFN-gamma, in the presence or absence of FBS. VEGF and IL-6 secretion were measured by ELISA. Inclusion of TNF-alpha significantly increased secretion of VEGF, whether or not IFN-gamma was present (Table 8).

TABLE 8

Secretion of VEGF (picograms/ml [pg/ml]) by ASC under various conditions.

| Expt. # | Cytokines | FBS | VEGF in CM/ RPD* | VEGF in bioreactor medium/ RPD* |
|---|---|---|---|---|
| 1 | TNF + IFN | NO | 619/3 | 195/3 |
|   | None | NO | 274/7 | 65/0 |
| 2 | TNF + IFN | NO | 7540/1 | 151/3 |
|   | None | NO | 3266/4 | 140/3 |
| 3 | TNF + IFN | YES | 371/3 | 1749/2 |
|   | TNF | YES | 370/10 | 1128/5 |
| 4 | TNF + IFN | YES | NT (not tested) | 373/2 |
|   | TNF | YES | NT | 348/8 |
| 5 | TNF + IFN | NO | 732 ± 20** | (not performed) |
|   | None | NO | 650 ± 46** | (not performed) |

*In this table and throughout the document, RPD refers to the percentage difference between duplicate samples in the ELISA.
**Indicated number is the standard deviation.

In the same experiment, inclusion of TNF-alpha significantly increased IL-6 secretion, which was further increased by IFN-gamma, as shown in Table 9.

TABLE 9

Secretion of IL-6 (picograms/ml [pg/ml]) by ASC under various conditions.

| Expt. # | Cytokines | FBS | IL-6 in CM | RPD |
|---|---|---|---|---|
| 1 | TNF + IFN | NO | 77 | 2 |
|   | None | NO | 10 | 2 |
| 2 | TNF + IFN | NO | 509* | 1 |
|   | None | NO | 40 | 4 |
| 3 | TNF + IFN | YES | 380 | 0 |
|   | TNF | YES | 92 | 14 |

*out of calibration curve.

Figure 7A:
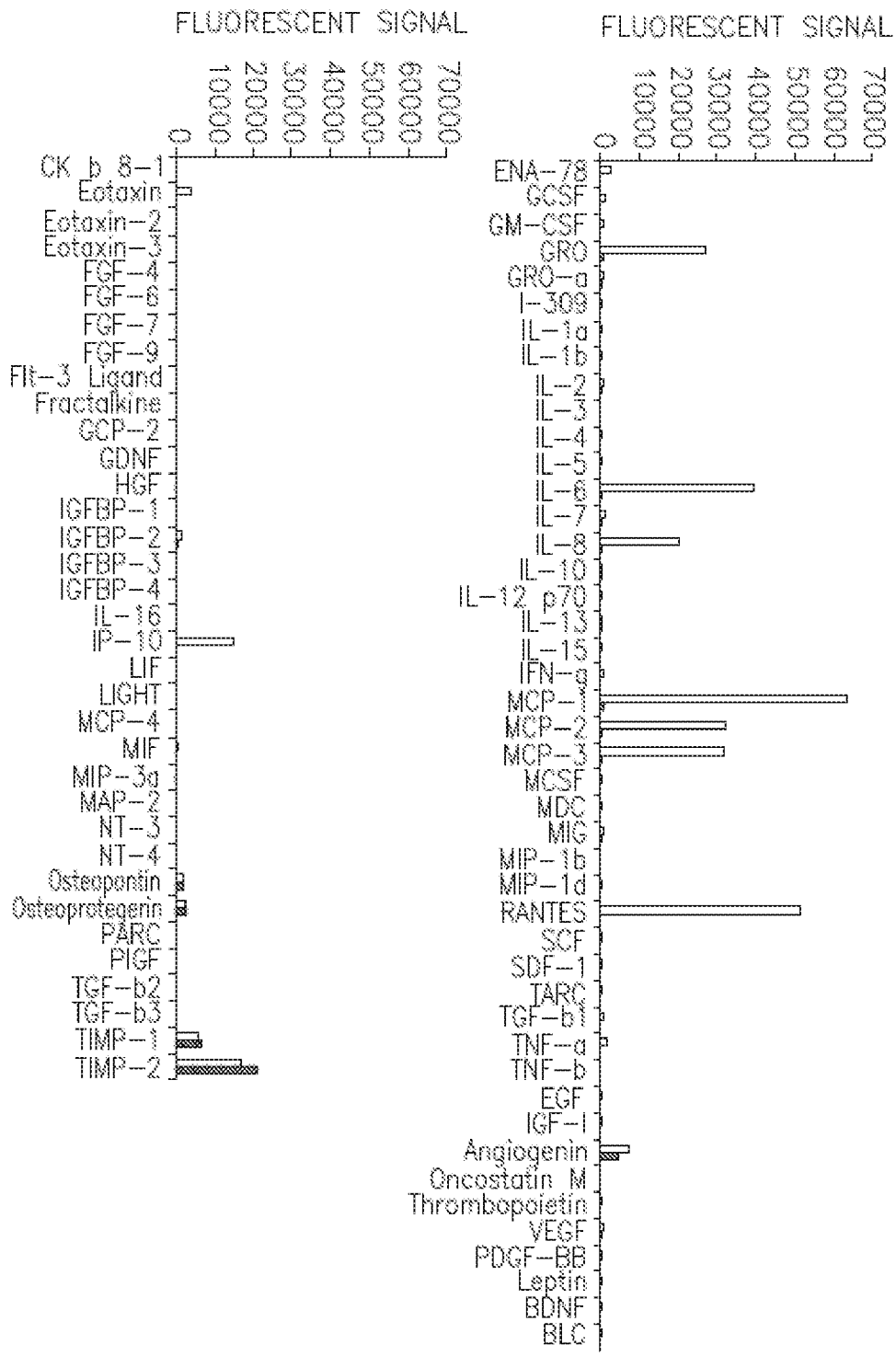
FIGS. 7A-B are graphs depicting secretion, measured by fluorescence, of various factors following incubation of ASC with TNF-alpha+IFN-gamma (unfilled bars) or control media (filled bars) in two separate experiments. C-D are graphs depicting fold-increase of secretion, measured by fluorescence, of GRO, IL-8, MCP-1, and RANTES (C), and IL-6, MCP-3, Angiogenin, Insulin-like Growth Factor Binding Protein-2 (IGFBP-2), Osteopontin, and Osteoprotegerin (D) following incubation of ASC with TNF-alpha alone, relative to incubation with control media (no cytokines).
Figure 7B:
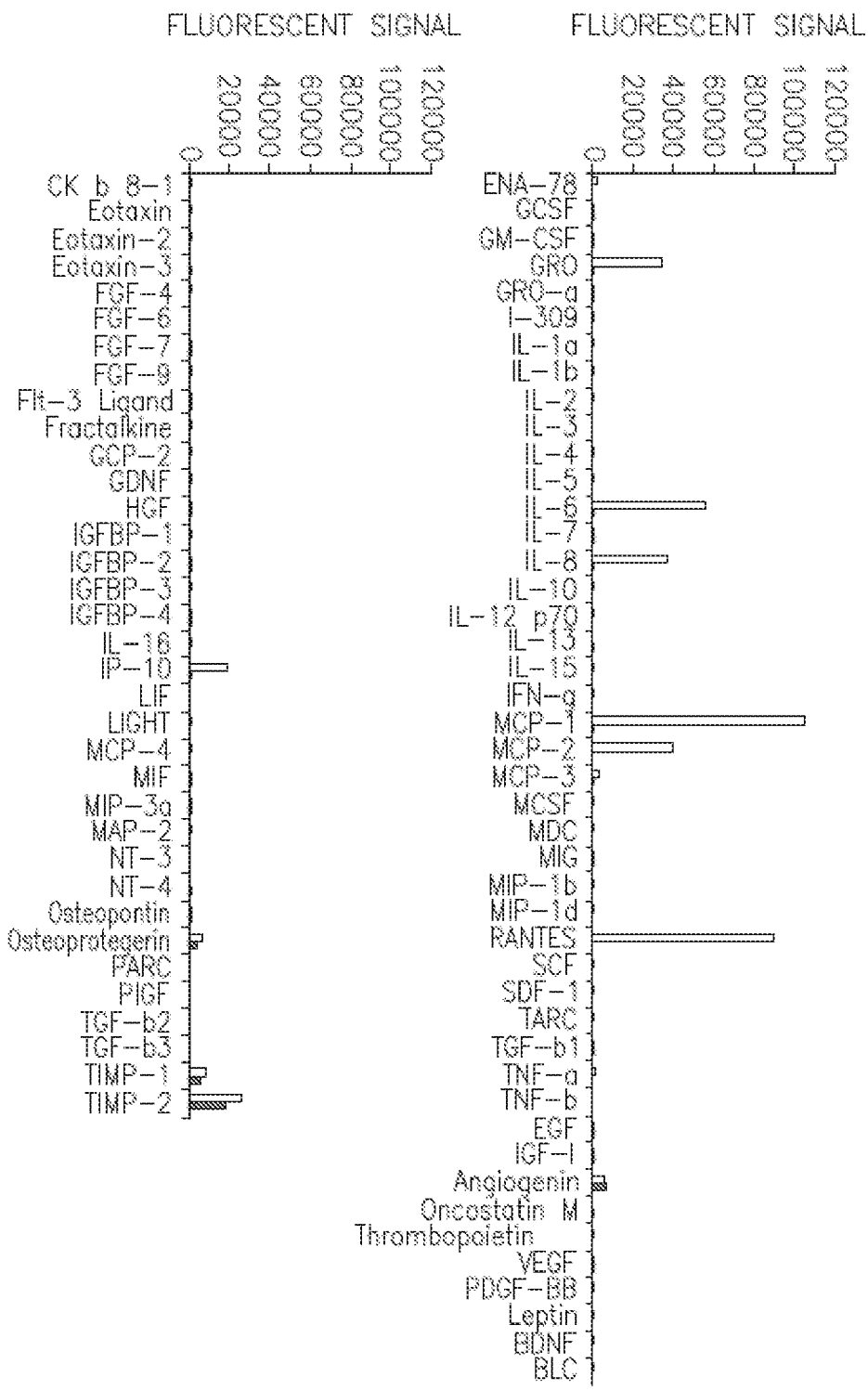
Figure 7C:
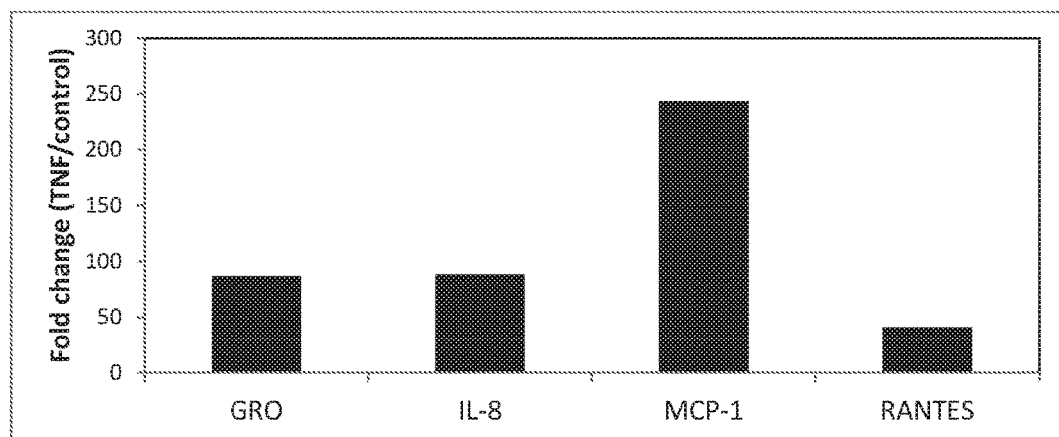
Figure 7D:
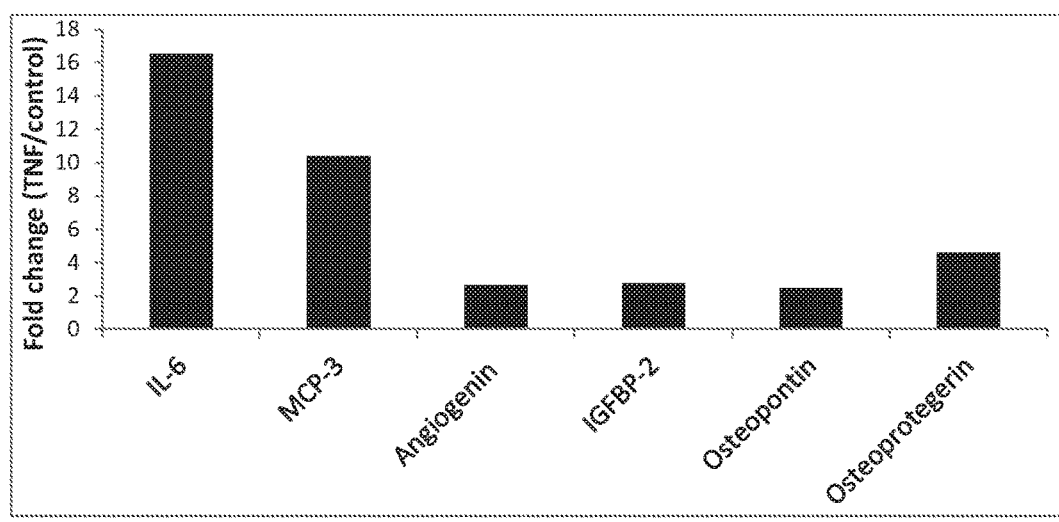

Expression of a panel of factors in the bioreactor media of Experiments 1-2 (see Tables 8-9), all performed in the absence of serum, was measured by a fluorescence-based cytokine array assay, revealing the increased expression of several factors, including GRO, IL-6, IL-8, MCP-1, MCP-2, MCP-3, RANTES, and IP-10 (Experiments 1-2 are shown in FIGS. 7A-B, respectively). In another experiment, TNF-alpha alone was compared to medium without cytokines (also in the absence of serum), showing increased expression of GRO, IL-8, MCP-1, RANTES, and, to a lesser extent, IL-6, MCP-3, Angiogenin, Insulin-like Growth Factor Binding Protein-2 (IGFBP-2), Osteopontin, and Osteoprotegerin (FIGS. 7C-D).

Figure 8A:
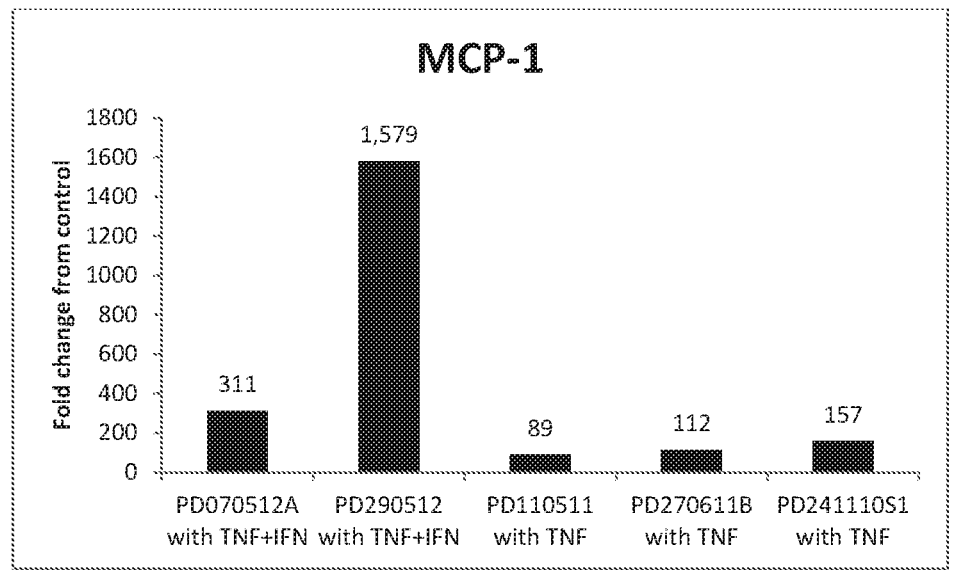
FIGS. 8A-B are graphs depicting fold-increase relative to control medium (containing no cytokines) in secretion of MCP-1 (A) and GM-CSF (B) in several experiments, as measured by ELISA.
Figure 8B:
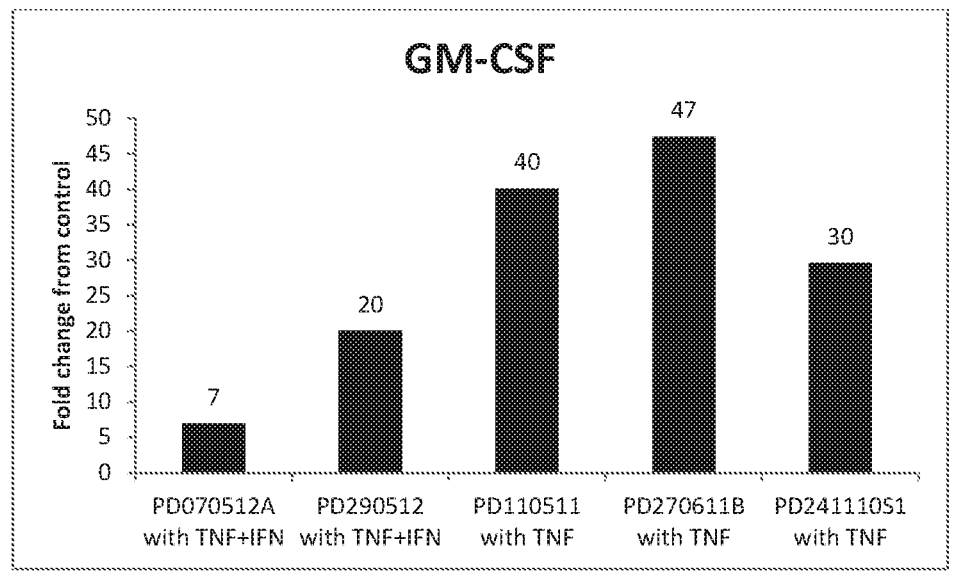

Increased expression of MCP-1 and GM-CSF in the bioreactor media was verified by quantitative ELISA in several experiments, all performed in the absence of serum. The results showed that TNF-alpha+IFN-gamma was superior to TNF-alpha alone for MCP-1 induction (FIG. 8A), while TNF-alpha alone appeared to be slightly superior for GM-CSF induction (FIG. 8B). The cytokine concentrations and fold-changes relative to control medium (containing no cytokines) from the TNF-alpha+IFN-gamma trial are shown in Table 10 below.

TABLE 10

MCP-1 and GM-CSF concentrations in bioreactor medium.

| Expt. No. | Conditions | MCP-1 in pg/ml/(fold-increase) | GM-CSF in pg/ml/(fold-increase) |
|---|---|---|---|
| 1 | TNF + IFN | 6365.4 (311) | 6.32 (6.9) |
|   | None | 20.5 | 0.91 |
| 2 | TNF + IFN | 9063.7 (1579) | 13.09 (20.0) |
|   | None | 5.8 | 0.65 |

The induction of several other factors, over several experiments utilizing TNF-alpha+IFN-gamma or TNF-alpha alone (all in the absence of serum), was detected by the aforementioned cytokine array. A number of proteins were consistently upregulated, a partial list of which is depicted in Table 11 below.

TABLE 11

Fold-enrichment (relative to no-cytokine control cells) of selected proteins upon incubation with TNF-alpha +/− IFN-gamma. Only fold-changes greater than 2 are depicted.

| Proteins | Condition/Expt. No. | | |
|---|---|---|---|
|  | TNF + IFN/ expt. 1 | TNF + IFN/expt. 2 | TNF alone/expt. 6 |
| ENA-78 | 13.0 | 11.4 |  |
| GCSF | 4.6 | 3.3 |  |
| GM-CSF | 3.7 | 3.1 |  |
| GRO | 57.8 | 102.7 | 87 |
| GRO-a | 2.9 | 2.5 |  |
| IL-2 | 3.8 | 3.2 |  |
| IL-6 | 199.2 | 281.4 | 16.5 |
| IL-7 | 4.6 | 2.5 |  |
| IL-8 | 32.6 | 80.5 | 88.7 |
| IL-10 | 3.2 | 3.5 |  |
| IFN-g | 2.9 | 2.8 |  |
| MCP-1 | 88.3 | 529.3 | 243.3 |
| MCP-2 | 88.3 | 198.5 |  |
| MCP-3 | 160.7 | 18.0 | 10.4 |
| MIG | 158.2 | 3.2 |  |
| RANTES | 4.4 | 452.1 | 41.3 |
| TGF-b1 | 256.7 | 3.5 |  |
| VEGF | 4.3 |  |  |
| Eotaxin | 17.6 | 2.1 |  |
| IGFBP-2 | 2.3 |  | 2.8 |
| IP-10 | 75.0 | 94.7 |  |
| MIF | 3.0 | 2.9 |  |
| Angiogenin |  |  | 2.7 |
| Osteopontin |  |  | 2.5 |
| Osteoprotegerin |  |  | 4.6 |

Example 8

Figure 9A:
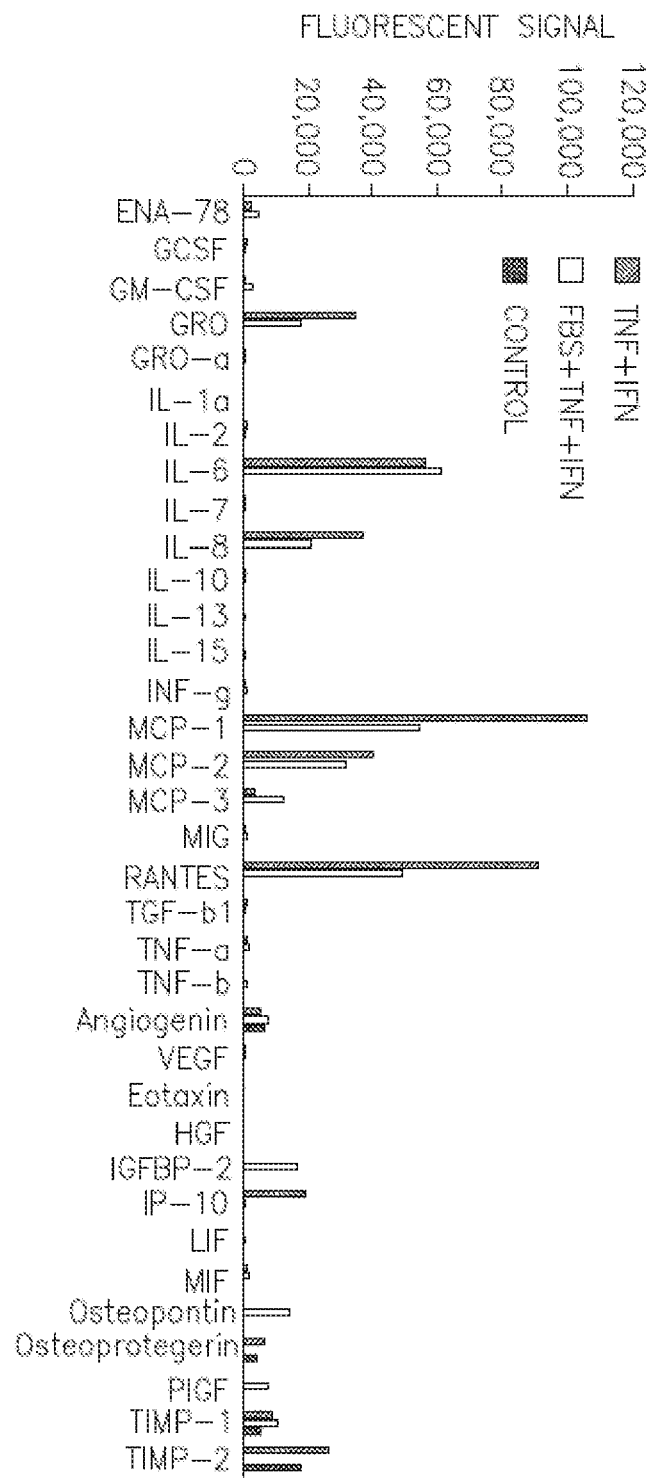
FIGS. 9A-B are graphs depicting secretion of various factors by TNF-alpha+IFN-gamma (A) or TNF-alpha alone (B) in the presence or absence of FBS. In (A), gray, white, and black bars indicate TNF-alpha+IFN-gamma; TNF-alpha+IFN-gamma+FBS; and control (no cytokines or serum), respectively. In (B), gray, white, and black bars indicate TNF-alpha alone; TNF-alpha+FBS; and control (no cytokines or serum), respectively.
Figure 9B:
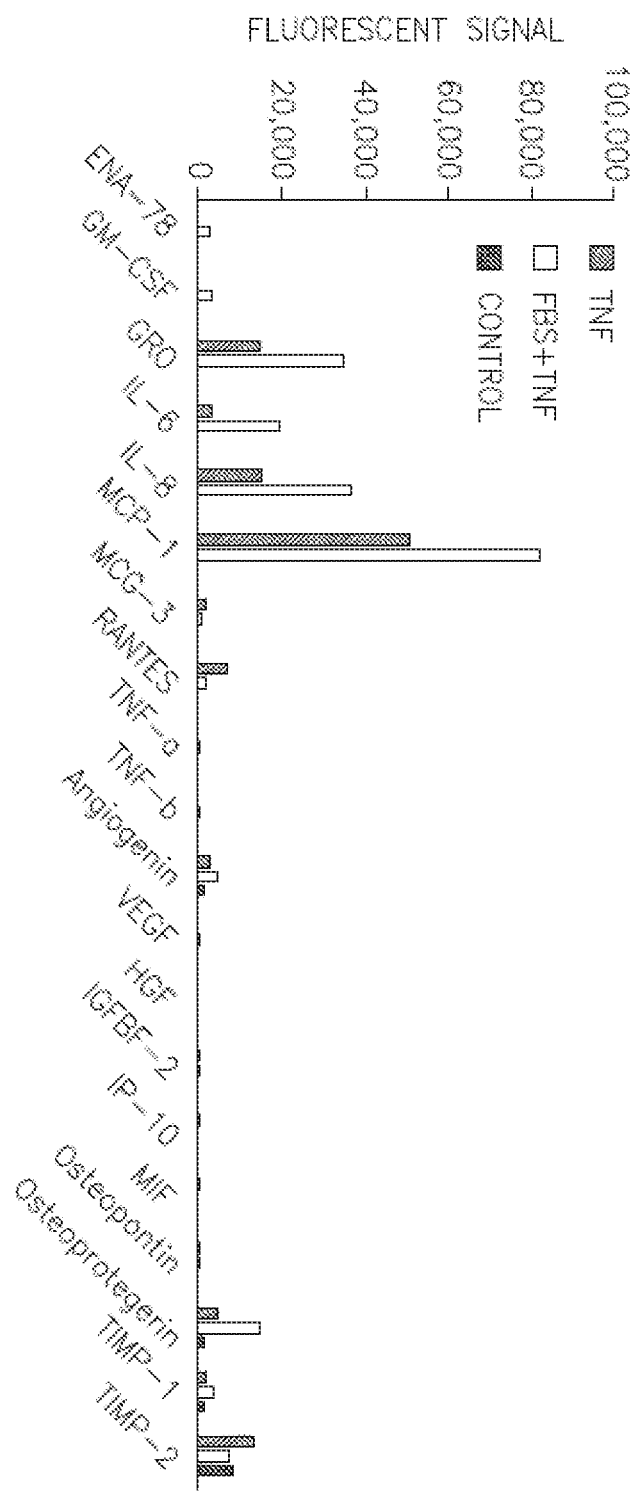

The Effect of Serum on Pro-Inflammatory Cytokine Treatment of ASC During 3D Culturing The next experiment examined the effect of FBS on induction of the aforementioned panel of factors by TNF-alpha+IFN-gamma (FIG. 9A) or TNF-alpha alone (FIG. 9B). A similar set of major proteins was induced in the presence or absence of FBS. In the case of TNF-alpha alone, IL-6 appeared to be induced much more strongly in the presence of FBS than in its absence.

Example 9

Immunomodulatory Effect of ASC Pre-Treated with Pro-Inflammatory Cytokines

Methods—PBMC IL-10 Secretion Assay

On day 1, 150,000 untreated ASC, pre-treated ASC, or control medium (no cells), in a volume of 150 microliters (mcL) were seeded in wells of a 48-well plate and were incubated overnight. On day 2, 50,000 human PBMC in a volume of 100 mcL were seeded into the wells containing ASC or control medium. On day 3, 1.5 micrograms (mcg) of LPS in 50 mcL medium was added to the cells, and the cells were incubated for 5 hours at 37° C. Cell-free supernatants were collected from the wells, and ELISA was performed using the Quantikine® ELISA Human IL-10 kit.

Results

The next experiment examined the effect of the pre-treated ASC on LPS-induced IL-10 secretion from PBMC. The pre-treated ASC elicited increased IL-10 secretion relative to untreated ASC.

Example 10

Quantitative Rantes Elisa on Pre-Treated ASC

ASC were incubated with 10 ng/ml TNF-alpha, alone or in combination with 10 ng/ml IFN-gamma, as described for Example 7. The cells were cryopreserved, then thawed, and then $5 \times 10^5$ cells were seeded in DMEM supplemented with 10% FBS and incubated under standard conditions. After 24 hours, the medium was replaced with 1-ml serum-free medium, and the cells were incubated another 24 hours under normoxic conditions. The medium was removed and assayed for RANTES secretion by ELISA, using the Quantikine® ELISA Human CCL5/RANTES kit (R&D Systems). The TNF-alpha+IFN-gamma-treated cells had sharply upregulated RANTES secretion compared to the other groups (Table 12).

TABLE 12

RANTES concentrations in culture medium.

| Expt. No. | Conditions | RANTES conc. | Standard dev. |
|---|---|---|---|
| 5 | No cytokines, no serum | 0 | 0 |
| 7 | No cytokines, serum. | 1 | 1 |
| 8 | No cytokines, serum | 0 | 0 |
| 5 | TNF-alpha, no serum | 75 | 2 |
| 7 | TNF-alpha, serum. | 577 | 20 |
| 8 | IFN-gamma + TNF-alpha + serum. | 3173* | 83 |

*Out of calibration curve.

Example 11

Immune-Phenotype of ASC Treated with Inflammatory Cytokines

The immune-phenotype of the ASC that had been pre-treated with pro-inflammatory cytokines was examined over several experiments. Consistently, the cells were over 90% positive for CD29, CD90, and CD54; over 85% positive for CD73 and CD105; and over 65% positive for CD49. Additionally, the cells were less than 1% positive for CD14, CD19, CD31, CD34, CD39, CD45, and HLA-DR; less than 3% were positive for CD200; less than 6% were positive for GlyA; and less than 20% were positive for SSEA4.

Example 12

ASC Pre-Treated with IFN-Gamma Alone

ASC are incubated with 10 ng/ml IFN-gamma alone, as described for Example 7. The cells are assayed as described in the above Examples.

Example 13

Effect of ASC on Muscular Dystrophy

Methods

Thirty three 4-week-old mdx male mice (Bulfield et al) were randomly divided into 3 groups. Animals were weighed, and each animal's forelimb force was measured by means of a grip strength meter. All groups underwent Rotarod™ running twice a week for 4 weeks to cause exercise-induced muscle damage, with the beginning of the exercise period considered day 1 of the study. The Rotarod™ accelerated from 5 to 45 rotations per minute within 15 seconds, and the session ended when a mouse ran for 500 seconds without falling. Two more attempts were made for mice that fell off within 500 seconds.

The mice were administered maternal-derived or fetal derived ASC intramuscularly (IM) at days 15 and 29. In both dosing sessions, the respective ASC populations were administered in a constant concentration of $10 \times 10^6$ cells/ml and at volume of 50 µl/injection in each thigh muscle (total of 100 µl/animal), resulting in dose of $1 \times 10^6$ cells/animal. For mice in the placebo group, 50 µl placebo was administered into each thigh muscle. Retro-orbital bleeding for creatine phosphokinase (CPK) measurement were done on study days 20 and 34 and at the end of the experiment. At day 42, the mice were sacrificed by carbon dioxide asphyxiation. Diaphragm and quadriceps muscle were harvested and fixed in formaldehyde for hematoxylin and eosin staining, for additional evaluation of inflammation, necrosis and regeneration levels. Evaluation was performed in a blinded fashion.

Results

Figure 10:
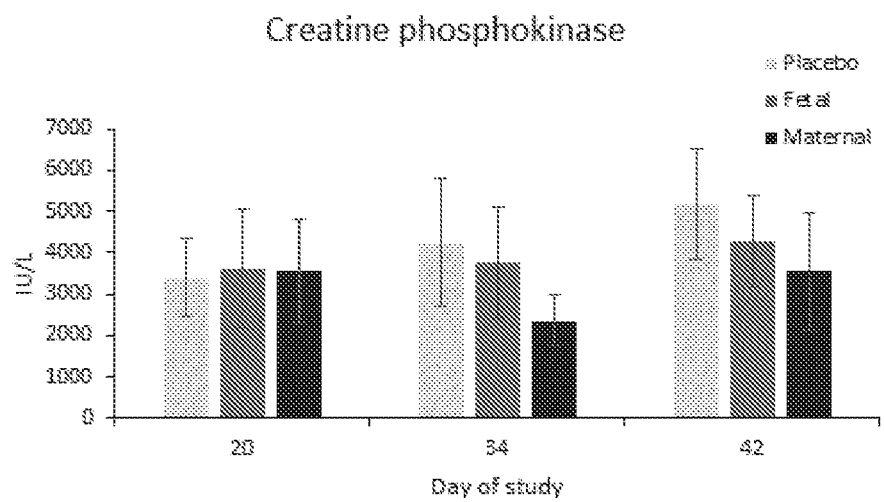
FIG. 10 is a graph showing CPK levels (international units/liter; vertical axis) in mice treated with placebo (negative control), fetal-derived ASC, or maternal-derived ASC at various timepoints (horizontal axis) after study initiation.
Figure 11A:
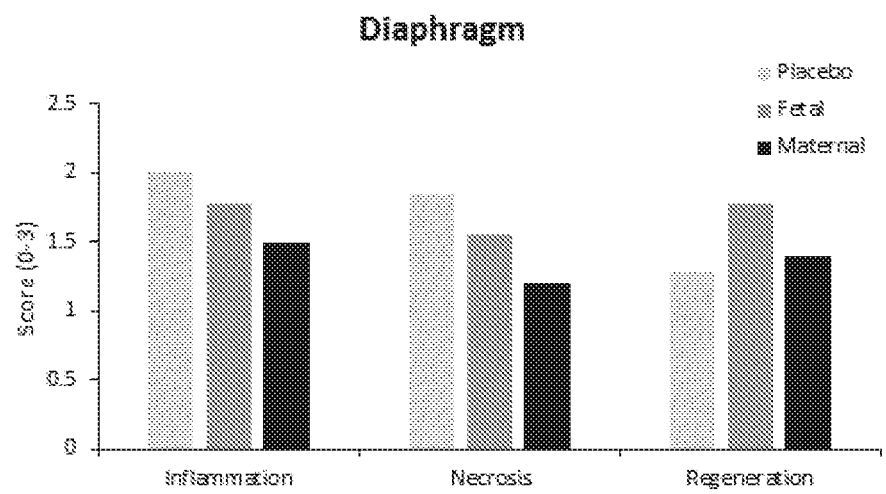
FIGS. 11A-B are graphs showing scores (vertical axis) for inflammation, necrosis, and regeneration (left, center, and right datasets, respectively) at the time of sacrifice in the diaphragm (A) and quadriceps (B).
Figure 11B:
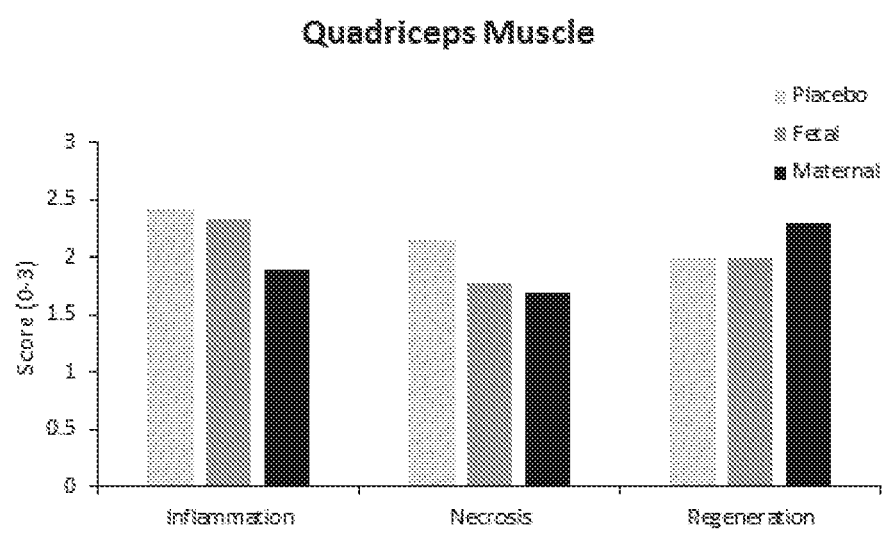

Both types of ASC reduced CPK levels on days 34 and 42. The improvement in the maternal ASC group was statistically significant over placebo at the 34-day timepoint by one sided T-Test; $t_{(15)}$=2.51, p=0.012 (FIG. 10). Furthermore, both types of ASC exhibited a trend of reduction of inflammation and necrosis in the diaphragm and quadriceps (FIGS. 11A-B, respectively).

In conclusion, ASC are therapeutically beneficial in subjects with muscular dystrophy.

Example 14

Effect of ASC and CM on Muscle Wasting Secondary to Heart Failure

Overview

Conditioned media (CM) from placental ASC is tested for ability to inhibit or reverse muscle wasting in subjects with heart failure, for example as described below. In other experiments, the tested ASC are placental ASC that have been exposed to inflammatory cytokines, or are placental ASC that are predominantly fetal cells. In other experiments, conditioned media (CM) is tested instead of the ASC.

Protocol

ZSF1 obese rats are cardiometabolic animals that develop metabolic syndrome, diabetes and renal disease (Hamdani N et al, 2013); they were obtained from Charles River Laboratories (Wilmington, Mass.). Placental ASC The experiment includes 4 groups (as detailed in Table 13) of 9-week-old male ZSF1 obese rats. After a one-week laboratory adaptation period, animals underwent phenotypic evaluation, consisting of metabolic cage studies, blood sample collection and echocardiographic evaluation. At the ages of 16 and 18 weeks, ASC or vehicle (PlasmaLyte A) were intramuscularly or intravenously injected: intravenous injections contained $9.2 \times 10^6$ cells (or vehicle) in a 400-µl cell suspension, injected into the tail vein; intramuscular administrations also contained $9.2 \times 10^6$ cells (or vehicle) in a 400-µl cell suspension, 50% of which was injected into each leg.

At the age of 20 weeks, animals were sacrificed, and skeletal muscle samples were preserved in paraffin.

Skeletal muscle samples are tested to determine muscle mass. In some experiments, histology is performed to further characterize the extent of cachexia, for example as described in Doehner W et al, 2014, and the references cited therein. Increased muscle mass in the treated groups, or inhibition of loss of muscle mass relative to healthy controls, is evidence of efficacy.

TABLE 13

Experimental groups.

| Group No. | Route | Number of administrations | modality | No. animals |
|---|---|---|---|---|
| 1 | IV | 2 | ASC | 9 |
| 2 | IM | 2 | ASC | 9 |
| 3 | IV | 2 | PlasmaLyte A | 5 |
| 4 | IM | 2 | PlasmaLyte A | 4 |

Example 15

Effect of ASC and CM on Muscle Wasting in Aging Animals

Overview

Conditioned media (CM) from placental ASC is tested for ability to inhibit or reverse muscle wasting syndrome in aging subjects, for example as described below. In other experiments, the tested ASC are placental ASC that have been exposed to inflammatory cytokines. In other experiments, conditioned media (CM) is tested instead of the ASC.

Protocol

Healthy, 12-month old C57BL/6J MICE were administered maternal placental ASC, fetal placental ASC, or vehicle (PlasmaLyte A), every 4 weeks from 12 months through 18 months. Injections were intramuscular, split evenly between the left and right Gracilis muscles, and contained a total of $1 \times 10^6$ cells in a 50-µl volume. The study was continued for 3 months after the last injection, after which the mice were sacrificed by carbon dioxide asphyxiation, and skeletal muscle samples were preserved in paraffin.

The skeletal muscle samples are tested to determine muscle mass. In some experiments, histology is performed to further characterize the extent of sarcopenia, for example as described in Baracos V et al, 2013 and the references cited therein. Increased muscle mass in the treated groups, or inhibition of loss of muscle mass relative to younger animals, is evidence of efficacy.

Example 16

Effect of CM and ASC on Human Subjects with Muscle Wasting or Muscle Loss

Human subjects with a muscle wasting disorder (e.g. a muscular dystrophy), muscle wasting syndrome or muscle loss, for example as a result of congestive heart failure, aging, congenital causes, cancer, AIDS, COPD (chronic obstructive pulmonary disease), renal failure, severe burns, stroke, or chronic use of corticosteroids, are administered compositions comprising ASC or CM. Muscle mass and/or lean body mass, strength, and exercise capacity are assessed, for example as described in Zembroń-Łacny A et al 2014, and the references cited therein. Increased muscle/lean body mass, strength testing, or exercise capacity (e.g. 6 minutes walking distance or peak VO2) in the treated group is evidence of efficacy.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications, and Uniprot and GenBank Accession numbers mentioned in this specification are herein incorporated in their entirety by reference into the specification, to the same extent as if each individual publication, patent or patent application or Gen-Bank Accession number was specifically and individually indicated to be incorporated herein by reference. In addition, citation or identification of any reference in this application shall not be construed as an admission that such reference is available as prior art to the invention.

REFERENCES

Additional References are Cited in the Text

Baracos V et al, Clinical outcomes related to muscle mass in humans with cancer and catabolic illnesses. Int J Biochem Cell Biol. 2013 October; 45(10):2302-8.

Bulfield et al. 1984. X chromosome-linked muscular dystrophy (mdx) in the mouse. Proc Natl Acad Sci USA 81(4):1189-92

Clayton A et al, Analysis of antigen presenting cell derived exosomes, based on immuno-magnetic isolation and flow cytometry. J Immunol Methods. 2001; 247(1-2):163-74.

Crescitelli R et al, Distinct RNA profiles in subpopulations of extracellular vesicles: apoptotic bodies, microvesicles and exosomes. J Extracell Vesicles. 2013 Sep. 12; 2.

Doehner W et al, Metabolic impairment in heart failure: the myocardial and systemic perspective. J Am Coll Cardiol. 2014 Sep. 30; 64(13):1388-400.

Dominici et al. Minimal criteria for defining multipotent mesenchymal stromal cells. The International Society for Cellular Therapy position statement. Cytotherapy. 2006; 8(4):315-7.

Hamdani N et al, Myocardial Titin Hypophosphorylation Importantly Contributes to Heart Failure with Preserved Ejection Fraction in a Rat Metabolic Risk Model. Circulation: Heart Failure. 2013; 6: 1239-1249.

Mathias R A et al, Isolation of extracellular membranous vesicles for proteomic analysis. Methods Mol Biol. 2009; 528:227-42.

Mohler M L et al, Nonsteroidal selective androgen receptor modulators (SARMs): dissociating the anabolic and androgenic activities of the androgen receptor for therapeutic benefit. J Med Chem. 2009 Jun. 25; 52(12):3597-617.

Zembroń-Łacny A et al, Sarcopenia: monitoring, molecular mechanisms, and physical intervention. Physiol Res. 2014 Aug. 26. [Epub ahead of print]

What is claimed is:

1. A method of treating a Duchenne muscular dystrophy in a subject in need thereof, the method comprising administering to the subject adherent stromal cells (ASC), wherein said ASC: (i) originate from placenta tissue, (ii) are at least predominantly maternal cells, and (iii) have been cultured on a three-dimensional (3D) substrate, thereby treating the Duchenne muscular dystrophy.

2. The method of claim 1, further comprising the step of harvesting said ASC by removing said ASC from an apparatus where culturing on said 3D substrate was performed.

3. The method of claim 1, wherein culturing on said 3D substrate is performed in an apparatus that comprises a 3D bioreactor.

4. The method of claim 1, wherein culturing on said 3D substrate is performed in an apparatus that comprises a synthetic adherent material that is selected from the group consisting of a polyester, a polypropylene, a polyalkylene, a poly fluoro-chloro-ethylene, a polyvinyl chloride, a polystyrene, a polysulfone, a cellulose acetate, a glass fiber, a ceramic particle, a poly-L-lactic acid, and an inert metal fiber.

5. The method of claim 1, wherein said ASC have been incubated in a 2D adherent-cell culture apparatus prior to culturing on said 3D substrate.

6. The method of claim 1, wherein administering said ASC leads to one or more of the following: reduction of creatine phosphokinase levels in the subject, reduction of inflammation in a diaphragm of the subject, reduction of necrosis in a diaphragm of the subject, reduction of inflammation in quadriceps of the subject, or reduction of necrosis in quadriceps of the subject.

7. A method of reducing a loss of muscle mass in a subject with Duchenne muscular dystrophy, the method comprising administering to the subject adherent stromal cells (ASC), wherein said ASC: (i) originate from placenta tissue, (ii) are at least predominantly maternal cells, and (iii) have been cultured on a three-dimensional (3D) substrate, thereby reducing the loss of muscle mass in the subject with Duchenne muscular dystrophy.

8. The method of claim 7, further comprising the step of harvesting said ASC by removing said ASC from an apparatus where culturing on said 3D substrate was performed.

9. The method of claim 7, wherein culturing on said 3D substrate is performed in an apparatus that comprises a 3D bioreactor.

10. The method of claim 7, wherein culturing on said 3D substrate is performed in an apparatus that comprises a synthetic adherent material that is selected from the group consisting of a polyester, a polypropylene, a polyalkylene, a poly fluoro-chloro-ethylene, a polyvinyl chloride, a polystyrene, a polysulfone, a cellulose acetate, a glass fiber, a ceramic particle, a poly-L-lactic acid, and an inert metal fiber.

11. The method of claim 7, wherein said ASC have been incubated in a 2D adherent-cell culture apparatus prior to culturing on said 3D substrate.

12. The method of claim 7, wherein administering said ASC leads to one or more of the following: reduction of creatine phosphokinase levels in the subject, reduction of inflammation in a diaphragm of the subject, reduction of necrosis in a diaphragm of the subject, reduction of inflammation in quadriceps of the subject, or reduction of necrosis in quadriceps of the subject.

13. A method of treating muscle degeneration in a subject with Duchenne muscular dystrophy, the method comprising administering to the subject adherent stromal cells (ASC), wherein said ASC: (i) originate from placenta tissue, (ii) are at least predominantly maternal cells, and (iii) have been cultured on a three-dimensional (3D) substrate, thereby treating muscle degeneration in the subject with Duchenne muscular dystrophy.

14. The method of claim 13, further comprising the step of harvesting said ASC by removing said ASC from an apparatus where culturing on said 3D substrate was performed.

15. The method of claim 13, wherein culturing on said 3D substrate is performed in an apparatus that comprises a 3D bioreactor.

16. The method of claim 13, wherein culturing on said 3D substrate is performed in an apparatus that comprises a synthetic adherent material that is selected from the group consisting of a polyester, a polypropylene, a polyalkylene, a poly fluoro-chloro-ethylene, a polyvinyl chloride, a polystyrene, a polysulfone, a cellulose acetate, a glass fiber, a ceramic particle, a poly-L-lactic acid, and an inert metal fiber.

17. The method of claim 13, wherein said ASC have been incubated in a 2D adherent-cell culture apparatus prior to culturing on said 3D substrate.

18. The method of claim 13, wherein administering said ASC leads to one or more of the following: reduction of creatine phosphokinase levels in the subject, reduction of inflammation in a diaphragm of the subject, reduction of necrosis in a diaphragm of the subject, reduction of inflammation in quadriceps of the subject, or reduction of necrosis in quadriceps of the subject.

* * * * *